US012605470B2

(12) United States Patent
Matsunaga et al.

(10) Patent No.: US 12,605,470 B2
(45) Date of Patent: Apr. 21, 2026

(54) NANODROPLET WITH LAYER-BY-LAYER ASSEMBLY

(71) Applicant: Arizona Board of Regents on Behalf of the University of Arizona, Tucson, AZ (US)

(72) Inventors: Terry O. Matsunaga, Tucson, AZ (US); Pedro Alcaraz, Tucson, AZ (US); Russell S. Witte, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 956 days.

(21) Appl. No.: 17/778,733

(22) PCT Filed: Nov. 20, 2020

(86) PCT No.: PCT/US2020/061471
§ 371 (c)(1),
(2) Date: May 20, 2022

(87) PCT Pub. No.: WO2021/102240
PCT Pub. Date: May 27, 2021

(65) Prior Publication Data
US 2022/0409750 A1     Dec. 29, 2022

Related U.S. Application Data

(60) Provisional application No. 62/939,368, filed on Nov. 22, 2019.

(51) Int. Cl.
| | |
|---|---|
| *A61K 49/22* | (2006.01) |
| *B82Y 5/00* | (2011.01) |
| *B82Y 30/00* | (2011.01) |
| *B82Y 40/00* | (2011.01) |

(52) U.S. Cl.
CPC .............. *A61K 49/227* (2013.01); *B82Y 5/00* (2013.01); *B82Y 30/00* (2013.01); *B82Y 40/00* (2013.01)

(58) Field of Classification Search
CPC ........... A61K 51/1255; A61K 51/1244; A61K 51/1248; A61K 51/1251; A61K 49/227; A61K 49/225; A61K 49/222
See application file for complete search history.

(56) References Cited

U.S. PATENT DOCUMENTS

| | | | |
|---|---|---|---|
| 9,545,456 B2 | 1/2017 | Oraevsky et al. | |
| 2018/0099059 A1 | 4/2018 | Hossack et al. | |
| 2018/0272012 A1 | 9/2018 | de Gracia Lux et al. | |
| 2018/0344849 A1* | 12/2018 | Trouard ................. | A61K 9/107 |

FOREIGN PATENT DOCUMENTS

| | | |
|---|---|---|
| CN | 106267241 A | 1/2017 |
| CN | 108815524 A | 11/2018 |
| WO | 2012048335 A2 | 4/2012 |

OTHER PUBLICATIONS

Cavalli et al (Micro- and nanobubbles: A versatile non-viral platform for gene delivery, International Journal of Pharmaceutics, 437-445, 2013 (Year: 2013).*
Ramasamy et al (Layer-by-layer assembly of liposomal nanoparticles with PEGyated polyelectrolytes enhances systemic delivery of multiple anticancer drugs, Acta Biomaterialia 10, 5116-5127, 2014 (Year: 2014).*
International Search Report for PCT/US20/61471 mailed Feb. 22, 2021.
Borges, et al., "Molecular interactions driving the layer-by-layer assembly of multilayers".
Forier, et al., "Lipid and polymer nanoparticles for drug delivery to bacterial biofilms".
Sheeran, et al., "Decafluorobutane as a phase-change contrast agent for low-energy extravascular ultrasonic imaging".
Rawtani, et al., "Emerging strategies and applications of layer-by-layer self-assembly", Nanobiomedicine, Jan.-Dec. 2014; 1:8.
Hadinger, et al., Optimization of phase-change contrast agents for targeting MDS-MB-231 Breast Cancer Cells, Ultrasound Med Biol. Dec. 2018; 44(12).
Toumia, et al., "Phase change ultrasound contrast agents with photopolymerized diacetylene shell", ACS Publications, May 1, 2019.
Lin, et al., "Optically and acoustically triggerable sub-micron phase-change contrast agents for enhanced photoacoustic and ultrasound imaging", PubMed, Photoacoustics, Apr. 11, 2017.

* cited by examiner

*Primary Examiner* — Micah Paul Young
(74) *Attorney, Agent, or Firm* — Thomas | Horstemeyer, LLP

(57) ABSTRACT

The present disclosure provides novel modified nanodroplets with a layerby-layer (LBL) assembly formulation ("LBLnNDs"). The LBLnNDs of the present disclosure comprise gaseous perfluorocarbon core, polymer shell, and multiple alternating positively and negatively charged biopolymer layers dispersed layerby-layer onto the shell of the LBLnNDs. Methods of making and use of the LBLnNDs are also provided.

20 Claims, 7 Drawing Sheets

NANODROPLET WITH LAYER-BY-LAYER ASSEMBLY

CROSS-REFERENCE TO RELATED APPLICATIONS

This application is a 35 U.S.C. § 371 U.S. national phase application claiming the benefit of, and priority to, PCT international application No. PCT/US2020/061471 filed on Nov. 20, 2020, which claims priority to, and the benefit of, U.S. provisional application entitled "NANODROPLET WITH LAYER-BY-LAYER ASSEMBLY" having Ser. No. 62/939,368, filed Nov. 22, 2019, the contents of both applications are hereby incorporated by reference in their entireties.

STATEMENT OF GOVERNMENT INTEREST

This invention was made with government support under Grant No. R21 CA185684 awarded by National Institutes of Health. The government has certain rights in the invention.

FIELD OF INVENTION

The present disclosure relates generally to modulate a nanodroplet with layer-by-layer assemblies to increase thermal stability but maintain acoustic activation at a similar power level compared to the non-layered counterpart.

BACKGROUND OF INVENTION

Over half a century ago, air bubbles were discovered to enhance ultrasound imaging when injected into the ventricular chamber of the heart. Since then, the use of gas-filled, stabilized, biocompatible microbubbles has been routinely used for contrast enhanced ultrasound (CEUS) and is the topic of many reviews, primarily involving contrast echocardiography. More recently, advances to the field were made with the introduction of phase-shift or phase-change contrast agents (PCCAs) whereby ultrasound-mediated acoustic droplet vaporization (ADV) converts the perfluorocarbon-filled droplet into a microbubble for diagnostic imaging. PCCAs have been identified as potential therapeutics for vascular occlusion via the ADV of droplets. To date, PCCAs have been used pre-clinically in animal models as ultrasound contrast agents where their properties make them potentially attractive candidates for a variety of other diagnostic and therapeutic applications, including high resolution/high intensity contrast enhanced ultrasound drug-delivery systems, diagnosis and treatment of cancerous and inflammatory diseases, etc. Of interest to the authors of this publication is the potential for extravascular imaging. This has already been reported by Choudhury and coworkers for imaging of myocardial scar tissue post-infarct. In order to translate this technology from lab to bench it has become apparent that greater control over the thermal and acoustic stability of PCCAs is necessary.

PCCA's are typically composed of a condensed perfluorocarbon (PFC) gas core, stabilized by a coating material such as hydrocarbon-surfactants, fluoro-surfactants or polymers. The core of PCCAs typically dictates the physical properties of the particle. PFC-PCCA in a condensed-liquid phase tend to be smaller in size—submicron in most instances, with an improved circulation half-life, and increased thermal and acoustic stability—when compared to PFC particles in a gaseous phase. The increased thermal and acoustic stability can be attributed to increased Laplace pressure experienced by the liquid phase particle, as well as the amphiphobic qualities of the PFC core; where it becomes kinetically favorable for a particle to remain in the condensed state even when the surrounding media's temperature surpasses the boiling point of the PFC. However, liquid phase PCCAs are difficult to image via ultrasound as they scatter ultrasound weakly compared to gaseous phase PCCAs. Thus, control over thermally and acoustically induced phase-transitions in PFC-PCCAs is important for the development of the aforementioned potential clinical applications. Studies have shown that PFC-PCCA are stable enough to allow for induced ADV using FDA approved mechanical indices in vivo. Although the thermal stability of PFC-PCCAs is suitable for imaging purposes; achieving thermal stabilization long enough for potential extravascular applications has proven difficult to achieve.

With a slight deviation from literature in the formulation of PFC-PCCAs, it has been demonstrated that volatile PFCs can be used to generate stable, submicron, PCCAs. These particles have shown decreased ultrasound vaporization thresholds (meeting FDA requirements of a MI<1.9 for clinical use) both in vitro and in vivo. The formulation of such particles has since been modified and refined with several processes including sonication, extrusion, homogenization, microfluidics, and condensation. However, the thermal stability of volatile PFC nanodroplets has remained an issue: wherein using more volatile PFC agents to reduce ADV thresholds results in the decreased thermal stability both in-vitro and in-vivo. On the other hand, using less volatile PFCs to increase thermal stability, results in an increase in ADV thresholds making volatile PFC-NDs a non-viable clinical option.

Recent work in the field of PCCAs have been directed towards understanding particle stability; both thermal and acoustic. One avenue of investigation has revolved around volatile PFC-ND and PFC-ND membrane modifications. Of note, more recent research papers have achieved stabilization via: 1) the introduction of acyl chain phospholipids; 2) polymerization of an alkene-modified block for secondary thiol-ene cross-linking or an amphiphilic 10,12-pentacosadiynoic acid (PCDA) shell covalently cross-linked with ultraviolet (UV) irradiation; 3) complete membrane modification to mimic bacterial cell envelopes; and, 4) increasing the molar percentage of PEGylated lipid thereby reducing the size and size variance of the PFC-NDs. Other investigations have focused on modifications to: 1) the PFC core, where in one case utilizing a mixture of high and low boiling point perfluorocarbons has generated an increase in thermal stability; and, 2) modification to the overall particle population properties, where decreasing polydispersity to make a more stable ensemble of nanodroplets using small volume micro-fluidization. However, detailed assessment of particle stability and its thermal/acoustic sensitivity has been infrequent.

Recent publications, both in-vivo and in-vitro, have demonstrated that the coating of PFC-ND membranes with soft biopolymers can have a net positive effect on the thermal stability of the PCCAs whilst allowing for highly functionalized outer membrane surfaces. It has been shown that coating perfluoropentane droplets with cellulose nanofibers altered the thermal and acoustic properties of the particles and coating perfluorooctyl bromide droplets with PEGylated-polyelectrolytes allowed for the tailorable stability in-vivo as well as tailorable interaction with phagocytic cells. However, despite quite encouraging stabilizing modifications, these publications did not consider highly volatile PFC-PCCAs (i.e. perfluorobutane), nor do they specifically or quantitatively address the relationship between thermal and acoustic stability. Addressing changes to PCCA stability and acoustic activation using more volatile perfluorocarbons may offer added benefits to PFC-NDs that may require ultrasound outputs more aligned for clinical application.

SUMMARY OF THE INVENTION

The present disclosure provides novel modified nano-droplets and/or nanoparticles with a layer-by-layer (LBL) assembly formulation (collectively referred as "LBLnNDs" or "LBLx-NDs"). The LBLnNDs or LBLx-NDs of the present disclosure comprise multiple, alternating charge, biopolymers layers, which stabilize the core membrane of the nanodroplets/nanoparticles so as to increase thermal stability, but remain acoustic (e.g., ultrasound) activation.

In certain embodiments, the present disclosure provides modified nanodroplets comprising decafluorobutane (DFB-NDs) gas phase-change contrast agents (PCCA) with a layer-by-layer (LBL) approach to the stabilization of the core membrane of the nanodroplets. However, other volatile gases may be applicable for use as well (i.e. octafluoropropane). In certain embodiments, up to 20 layers of alternating positive and negatively charged biopolymers were successfully applied onto the DFB-ND membrane surface, and the resulting modified nanodroplets were analyzed by sizing and zeta potential. In other embodiments, the present disclosure provides studies for thermal stability and ultrasound activation of the nanodroplets comprising the DFB-NDs with a six (6) alternating negative and positively charged biopolymers, as compared to the corresponding non-layered nanodroplets as control. Results indicated at 37° C. and 45° C., the half-life of the LBLnNDs were 76.17 and 33.65 hours, 80.60 and 29.62 hours for $LBL_{10}NDs$, and 53.32 hours and 12.16 hours for the corresponding non-layered DFB-NDs controls. In addition, an activation profile as a function of ultrasound activation potential indicated no significant change in activation output requirements for the $LBL_6$-NDs and $LBL_{10}NDs$ nanodroplets vs. the non-layered nanodroplet control. These results are consistent with the $LBL_6$-NDs and $LBL_{10}NDs$ nanodroplets imparting thermal stability but not statistically altering ultrasound activation requirements.

BRIEF DESCRIPTION OF THE DRAWINGS

FIG. 3A. Droplet size vs. number of layers. FIG. 3B. Zeta potential as a function of number of layers. Zeta potential reflects net charge of the outermost polyelectrolyte/ND layer.

FIG. 4A. Vials of droplets incubated at 45° C. after 3 days. Note $LBL_6$-NDs appear opaque (right side) while control DFB-NDs appear clearer (left side). FIG. 4B. Ultrasound image of same samples exposed to identical ultrasound insonation using a split chamber. Left side of screen: DFB-NDs. Right: $LBL_6$-NDs. Note significant number of acoustic vaporization events (ND to MB transition) produced from HIFU pulse in the right-hand side ($LBL_6$-NDs) of the image whilst the left side (DFB-NDs) is devoid of MBs.

FIG. 5A. Demonstration of acoustic vaporization (transition between ND to MB) limited to chamber dimensions for selective insonation lateral beam region. FIG. 5B. Frame by frame correlation diagram, encircled red points demonstrate frames where there is a low frame to frame correlation; these frames are the locations of HIFU ND activation. FIG. 5C. Simple image processing routine quantifying number of ND vaporization events within lateral beam field. Relative contrast provided by DFB-NDs and $LBL_6$-NDs measured in number of vaporization events as a function mechanical index.

(FIG. 6A) and 45° C. (FIG. 6B). Data was obtained for at 0, 24, 72, 96, 120, &144 hours (37° C.) and 0, 12, 24, 36, 48, 72, & 96 hours (45° C.) of incubation for emulsions of DFB-NDs vs. $LBL_6$-ND and $LBL_{10}$-NDs (N=8 each). Acoustic vaporization curves after (A) 0, 72, and 120 hrs. incubation for (37° C.) and (B) 0, 24, and 48 hrs. incubation for (37° C.) were shown here.

(FIG. 7A) and 45° C. (FIG. 7B). Quantification of ultrasound-mediated ND vaporization measured as a function of time after inoculation at ambient pressure and times designated. Data comes from acoustic vaporization of NDs at MI=1.09, each curve contains N=8 samples.

(FIG. 8B) Linear portion of the acoustic vaporization fitted curves demonstrate that $LBL_6$-NDs and $LBL_{10}$-NDs slopes are within the 95% confidence interval of the slope for the DFB-NDs.

DETAINED DESCRIPTION OF THE INVENTION

Figure 1:
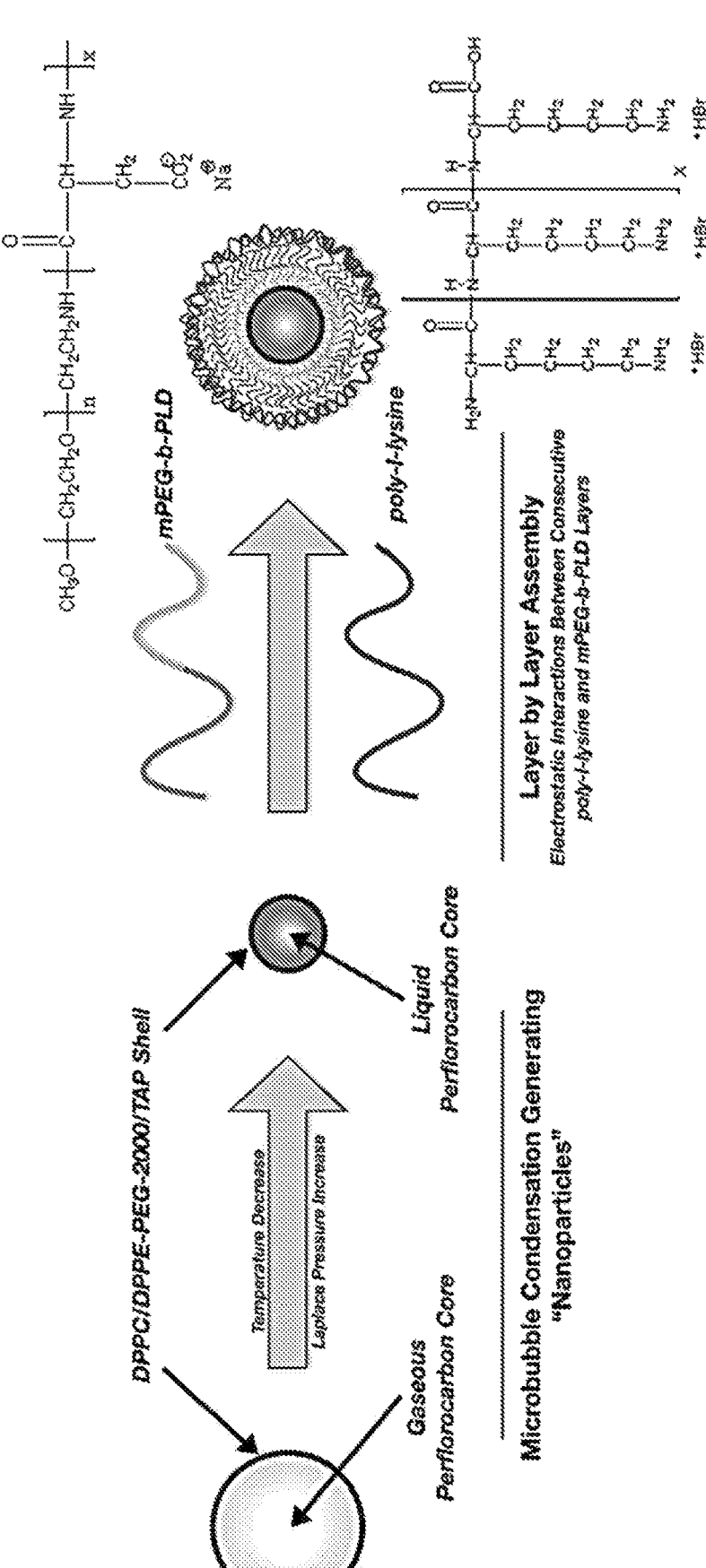
FIG. 1. Schematic of LBL-ND formation. Decaflourobutane nanodroplets (DFB-NDs) were generated using the condensation method [Sheeran et al., 2017], followed by deposition of alternating layers of polymeric polyelectrolytes onto the nanodroplet surface. Gentle vortexing was applied to increase polymeric adhesion to the DFB-ND core and additionally to each subsequent layer.
Figure 2:
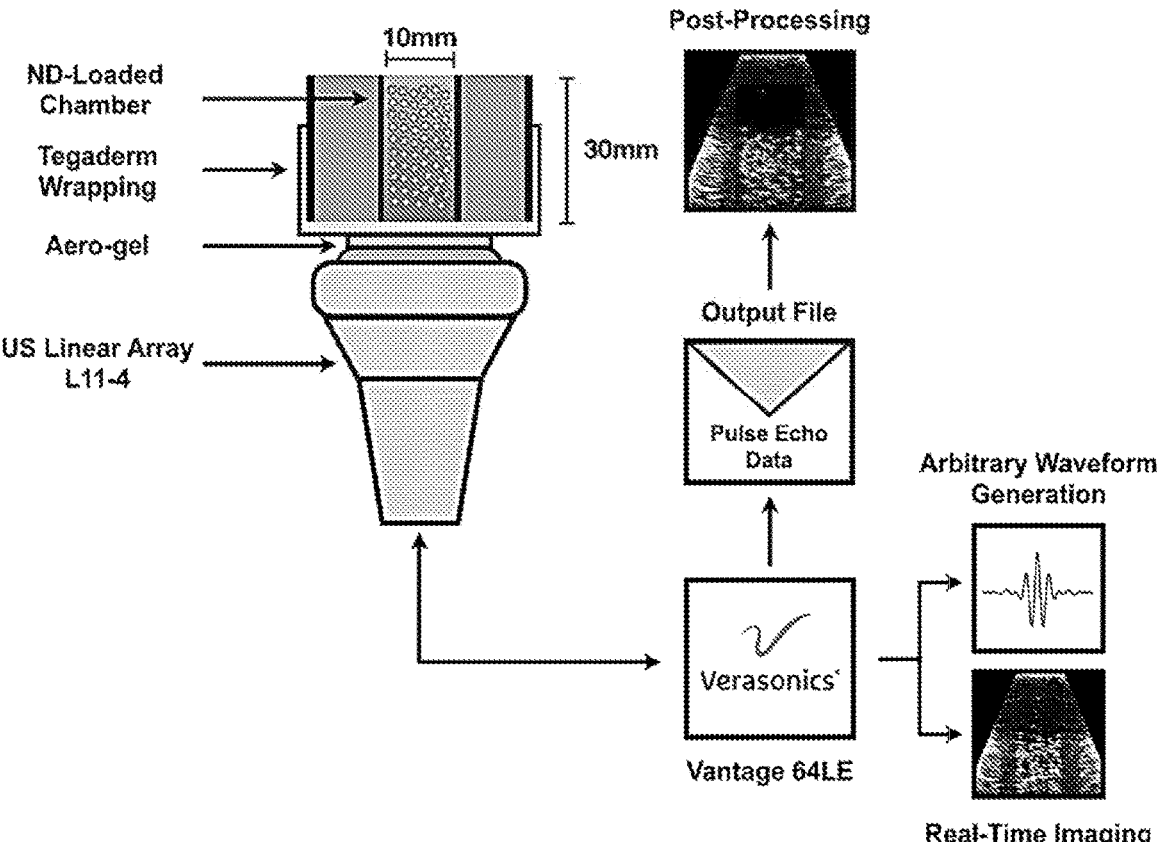
FIG. 2. Schematic for determining static vaporization thresholds. A window chamber was designed in Solid-works™ for holding one or more ND samples. An acoustic window made of 3M Tegaderm™ with gel was placed at the bottom for coupling ultrasound into the chamber. The Vantage 64LE and L11-4 transducer (Visualsonics, Toronto, Ca) delivered ultrasound pulses with varying pressure to vaporize NDs. Plane wave beam-formed data was collected and saved. A MATLAB algorithm was used offline to quantify the activation events as described in the methods.

Before the present disclosure is described in greater detail, it is to be understood that this disclosure is not limited to particular embodiments described, and as such may, of course, vary. It is also to be understood that the terminology used herein is for the purpose of describing particular embodiments only and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of nanotechnology, organic chemistry, formulations chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims.

The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The terms "treating" or "preventing", as used herein, can include preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

The terms "bioactive agent" and "active agent", as used interchangeably herein, include, without limitation, physiologically, pharmacodynamically, pharmaceutically, pharmacokinetically, or pharmacologically active substances that act locally or systemically in the body. A bioactive agent is a substance used for the treatment (e.g., therapeutic agent), prevention (e.g., prophylactic agent), management, palliation, and/or diagnosis (e.g., diagnostic agent), cure or mitigation of disease or illness, a substance which affects the structure or function of the body, or pro-drugs, which become biologically active or more active after they have been placed in a predetermined physiological environment.

The terms "sufficient" and "effective", as used interchangeably herein, refer to an amount (e.g. mass, volume, dosage, concentration, and/or time period) needed to achieve one or more desired result(s) whether it be suprapharmacologic, for instance, or subpharmacologic and spanning the range in between the two parameters.

The term "biocompatible", as used herein, refers to a material that along with any metabolites or degradation products thereof that are generally non-toxic to the recipient and do not cause any significant adverse effects to the recipient. Generally speaking, biocompatible materials are materials that do not elicit a significant inflammatory or immune response when administered to a patient.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "pharmaceutically acceptable", as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. A "pharmaceutically acceptable carrier", as used herein, refers to all components of a pharmaceutical formulation which facilitate the delivery of the composition in vivo. Pharmaceutically acceptable carriers include, but are not limited to, diluents, preservatives, binders, lubricants, disintegrators, swelling agents, fillers, stabilizers, and combinations thereof.

The term "molecular weight", as used herein, generally refers to the mass or average mass of a molecule making up a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

The term "small molecule", as used herein, generally refers to an organic molecule that is less than about 2000 g/mol in molecular weight, less than about 1500 g/mol, less than about 1000 g/mol, less than about 800 g/mol, or less than about 500 g/mol. Small molecules are non-polymeric and/or non-oligomeric.

The term "copolymer" as used herein, generally refers to a single polymeric material that is comprised of two or more different monomers. The copolymer can be of any form, such as random, block, graft, etc. The copolymers can have any end-group, including capped or acid end groups.

The term "hydrophilic", as used herein, refers to substances that have strongly polar groups that are readily soluble in water.

The term "hydrophobic", as used herein, refers to substances that lack an affinity for water; tending to repel and not absorb water as well as not dissolve in or mix with water.

The term "lipophilic", as used herein, refers to compounds having an affinity for lipids.

The term "amphiphilic", as used herein, refers to a molecule combining hydrophilic and lipophilic (hydrophobic) properties.

The term "mean particle size", as used herein, generally refers to the statistical mean particle size (diameter) of the particles in the composition. The diameter of a spherical or substantially spherical particle may be referred to as the physical or hydrodynamic diameter. The diameter of a non-spherical particle may refer preferentially to the hydrodynamic diameter. As used herein, the diameter of a non-spherical particle may refer to a linear distance between two points on the surface of the particle. Mean particle size can be measured using methods known in the art, such as dynamic light scattering. Two populations can be said to have a "substantially equivalent mean particle size" when the statistical mean particle size of the first population of nanoparticles is within 20% of the statistical mean particle size of the second population of nanoparticles; more preferably within 15%, most preferably within 10%.

The terms "monodisperse" and "homogeneous size distribution", as used interchangeably herein, describe a population of particles, microparticles, or nanoparticles all having the same or nearly the same size. As used herein, a monodisperse distribution refers to particle distributions in which 90% of the distribution lies within 5% of the mean particle size.

The term "targeting moiety", as used herein, refers to a moiety that binds to or localizes to a specific locale. The moiety may be, for example, a protein, nucleic acid, nucleic acid analog, carbohydrate, or small molecule. The locale may be a tissue, a particular cell type, or a subcellular compartment. The targeting moiety or a sufficient plurality of targeting moieties may be used to direct the localization of a particle or an active entity. The active entity may be useful for therapeutic, prophylactic, or diagnostic purposes.

The term "reactive coupling group", as used herein, refers to any chemical functional group capable of reacting with a second functional group to form a covalent bond. The selection of reactive coupling groups is within the ability of the skilled artisan. Examples of reactive coupling groups can include primary amines ($-NH_2$) and amine-reactive linking groups such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these conjugates to amines by either acylation or alkylation. Examples of reactive coupling groups can include aldehydes ($-COH$) and aldehyde reactive linking groups such as hydrazides, alkoxyamines, and primary amines. Examples of reactive coupling groups can include thiol groups ($-SH$) and sulfhydryl reactive groups such as maleimides, haloacetyls, and pyridyl disulfides. Examples of reactive coupling groups can include photoreactive coupling groups such as aryl azides or diazirines. The coupling reaction may include the use of a catalyst, heat, pH buffers, light, or a combination thereof.

The term "protective group", as used herein, refers to a functional group that can be added to and/or substituted for another desired functional group to protect the desired functional group from certain reaction conditions and selectively removed and/or replaced to deprotect or expose the desired functional group. Protective groups are known to the skilled artisan. Suitable protective groups may include those described in Greene, T. W. and Wuts, P. G. M., Protective Groups in Organic Synthesis, (1991). Acid sensitive protective groups include dimethoxytrityl (DMT), tert-butylcarbamate (tBoc) and trifluoroacetyl (tFA). Base sensitive protective groups include 9-fluorenylmethoxycarbonyl (Fmoc), isobutyrl (iBu), benzoyl (Bz) and phenoxyacetyl (pac). Other protective groups include acetamidomethyl, acetyl, tert-amyloxycarbonyl, benzyl, benzyloxycarbonyl, 2-(4-biphenylyl)-2-propyloxycarbonyl, 2-bromobenzyloxycarbonyl, tert-butyls tert-butyloxycarbonyl, 1-carbobenzoxamido-2,2,2-trifluoroethyl, 2,6-dichlorobenzyl, 2-(3,5-dimethoxyphenyl)-2-propyloxycarbonyl, 2,4-dinitrophenyl, dithiasuccinyl, formyl, 4-methoxybenzenesulfonyl, 4-methoxybenzyl, 4-methylbenzyl, o-nitrophenylsulfenyl, 2-phenyl-2-propyloxycarbonyl, α-2,4,5-tetramethylbenzyloxycarbonyl, p-toluenesulfonyl, xanthenyl, benzyl ester, N-hydroxysuccinimide ester, p-nitrobenzyl ester, p-nitrophenyl ester, phenyl ester, p-nitrocarbonate, p-nitrobenzylcarbonate, trimethylsilyl and pentachlorophenyl ester.

The term "nanoparticle" as used herein refers to a polymeric particle, a lipid particle, a lipid-stabilized polymeric particle, a liposome, a solid lipid particle, an inorganic particle, or combinations thereof. The term "nanodroplet" as used herein refers to an amount of liquid that is encased or surrounded by a different, enclosing substance (e.g., lipid layer). As used herein, nanoparticles and nanodroplets can be used interchangeably.

The nanoparticle and/or nanodroplet may have any diameter. Nanodroplets in general have a diameter less than about 1.3 μm, 1.2 μm, 1.1 μm, 1.0 μm, 0.9 μm, 0.8 μm, 0.7 μm, 0.6 μm, 0.5 μm, 0.4 μm, 0.3 μm, 0.2 μm, 0.1 μm, or less. Nanoparticles can have a diameter of about 10 nm to about 10 microns, about 10 nm to about 1 micron, about 10 nm to about 500 nm, about 20 nm to about 500 nm, or about 25 nm to about 250 nm. In some embodiments the therapeutic, prophylactic, or diagnostic nanoparticle has a diameter from about 25 nm to 500 nm, about 50 nm to 500 nm, about 50 nm to 400 nm, about 60 nm to 400 nm, or about 100 nm to 400 nm.

The nanoparticle can have any zeta potential from −300 mV to +300 mV, −100 mV to +100 mV, from −50 mV to +50 mV, from −40 mV to +40 mV, from −30 mV to +30 mV, from −20 mV to +20 mV, from −10 mV to +10 mV, or from −5 mV to +5 mV. The nanoparticle can have a negative, a positive zeta potential, or a substantially neutral zeta potential, i.e. the zeta potential is approximately 0 mV. In some embodiments the nanoparticle has a zeta potential of approximately −20 mV to +20 mV, more preferably −10 mV to +10 mV.

The term "ultrasound", as used herein, refers generally to acoustic radiation with a frequency greater than about 20 kHz, 50 kHz (e.g., for preclinical use), 100 kHz, 500 kHz, 1,000 kHz, 5,000 kHz, 10,000 kHz, or greater. The ultrasound can be medical ultrasound, e.g. about 500 kHz to 30,000 kHz, about 1,000 kHz to 20,000 kHz, about 2,000 kHz to 15,000 kHz, or about 3,000 kHz to 10,000 kHz.

Layer-by-Layer Nanodroplet/Nanoparticle Assembly (LBLnNDs or LBLx-NDs)

The present disclosure provides novel modified nanodroplets and/or nanoparticles with a layer-by-layer (LBL) assembly formulations (collectively referred as "LBLnNDs" or "LBLx-NDs"), which comprise multiple, alternating charge, biopolymers layers. The LBLnNDs of the present disclosure stabilize the core membrane of the nanodroplets/nanoparticles so as to increase thermal stability, but remain acoustic (e.g., ultrasound) activation.

Phase change nanodroplet or nanoparticle with layer-by-layer (LBL) assembly, i.e., LBLnNDs are provided. In certain embodiments, the present disclosure provides modified nanodroplets comprising decafluorobutane (DFB-NDs) gas phase-change contrast agents (PCCA) with a layer-by-layer (LBL) approach to the stabilization of the core membrane of the nanodroplets. However, other volatile gases may be applicable for use as well (i.e. octafluoropropane). In certain embodiments, up to 20 layers of alternating positive and negatively charged biopolymers were successfully applied onto the DFB-ND membrane surface, and the resulting modified nanodroplets were analyzed by sizing and zeta potential.

The LBLnNDs can contain any of the above lipids, polymers or blends or copolymers thereof. The LBLnNDs can contain one, two, three, or more different lipids and/or polymers layers.

The polymers are preferably biodegradable, biocompatible, or a combination with non-biodegradable polymer matrix. Biodegradable polymers can include polymers that are insoluble or sparingly soluble in water that are converted chemically or enzymatically in the body into water-soluble materials. Biodegradable polymers can include soluble polymers crosslinked by hydrolyzable cross-linking groups to render the crosslinked polymer insoluble or sparingly soluble in water. Biodegradable polymers can include polyamides, polycarbonates, polyalkylenes, polyalkylene glycols, polyalkyl glycols polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly (isobutylmethacrylate), poly(hexylmethacrylate), poly(isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene and polyvinylpyrrolidone, derivatives thereof, linear and branched copolymers and block copolymers thereof, and blends thereof. Exemplary biodegradable polymers include polyesters, poly(ortho esters), poly(ethylene imines), poly(caprolactones), poly(hydroxybutyrates), poly(hydroxyvalerates), polyanhydrides, poly(acrylic acids), polyglycolides, poly(urethanes), polycarbonates, polyphosphate esters, polyphosphazenes, poly(alkylamines), derivatives thereof, linear and branched copolymers and block copolymers thereof, and blends thereof.

Non-biodegradable polymers can include ethylene vinyl acetate, poly(meth) acrylic acid, polyamides, copolymers and mixtures thereof.

The polymers can be hydrophilic polymers. Hydrophilic polymers include cellulosic polymers such as starch and polysaccharides; hydrophilic polypeptides; poly(amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly(hydroxyalkylmethacrylamide); poly(hydroxyalkylmethacrylate); poly(saccharides); poly(hydroxy acids); poly(vinyl alcohol), and copolymers or hybrids of one or more polymers or co-polymers thereof.

Examples of suitable hydrophobic polymers include polyhydroxyacids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); polycarbonates such as tyrosine polycarbonates; polyamides (including synthetic and natural polyamides), polypeptides, and poly(amino acids); polyesteramides; polyesters; poly (dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene); copolymers; polyketals; polyphosphates; polyhydroxyvalerates; polyalkylene oxalates; polyalkylene succinates; poly(maleic acids), as well as copolymers or hybrids of one or more polymers or co-polymers thereof. In certain embodiments, the hydrophobic polymer is an aliphatic polyester. In preferred embodiments, the hydrophobic polymer is poly(lactic acid), poly(glycolic acid), or poly (lactic acid-co-glycolic acid).

The molecular weight of the hydrophobic polymer can be varied to tailor the properties of the LBLnNDs. For example, the molecular weight of the hydrophobic polymer segment can be varied to engineer nanoparticles possessing the required average particle size and degradation profile. The hydrophobic polymer segment has a molecular weight of between about 150 Da and about 100 kDa, more preferably between about 1 kDa and about 75 kDa, most preferably between about 5 kDa and about 50 kDa.

The polymer can also be an amphiphilic polymer. Amphiphilic polymers can include block copolymers of any of the hydrophobic and hydrophilic polymers described above. In some embodiments the amphiphilic polymer is a copolymer containing a hydrophobic polyhydroxyacid block and a hydrophilic polyalkylene glycol block. The amphiphilic polymer can be a PLGA-PEG block copolymer, and PGA-PEG block copolymer, or a PLGA-PEG block copolymer.

The LBLnNDs contain phage change nanodroplets that can be a liquid at certain temperatures and pressures but can be stimulated/insonated to form a gas by an appropriate wavelength or wavelengths of ultrasound radiation. The phase change nanodroplet can contain a gas precursor core. The phase change nanodroplet can be encapsulated by an outer shell containing one or more lipids. The gas precursor can be a liquid at certain temperatures and pressures but can be stimulated to form a gas by an appropriate wavelength or wavelengths of ultrasound radiation.

The LBLnNDs contain phase change nanodroplets that can have any size suitable for the intended application. However, in some embodiments the phase change nanodroplets have a diameter of about 50 nm to 1.5 micron, about 75 nm to 1.5 micron, about 75 nm to 1 micron, about 100 nm to 1 micron, about 150 nm to 1 micron, about 150 nm to 800 micron, about 200 nm to 800 micron, about 200 nm to 500 nm, or about 300 nm to 500 nm.

The LBLnNDs contain phase change nanodroplets each contains a gas precursor. The gas precursor can be selected to have a boiling point such that the gas precursor is a liquid at a specific temperature and pressure when in the nanodroplet, but can be stimulated by radiation to become a gas thereby rupturing or expanding and reorganizing the outer shell encasing the phase change nanodroplet. The gas precursor can have a boiling point temperature of about −90° C. to 10° C., about −40° C. to 10° C., about −30° C. to 10° C., about −20° C. to 10° C., about −10° C. to 10° C., about −10° C. to 5° C., about −8° C. to 5° C., about −8° C. to 0° C., about −5° C. to 0° C., about −2° C. to 0° C., or about −2° C. to −1° C.

The gas precursor can be any molecule having the proper physical properties to be a liquid when encased in the outer shell of the nanodroplet but to be stimulated to a gas by the application of ultrasound frequencies of radiation. The gas precursor can be a fluorocarbon, e.g. a straight chain or branched chain fluorocarbon having from 1 to 20 carbon atoms, from 2 to 12 carbon atoms, from 2 to 10 carbon atoms, from 3 to 10 carbon atoms, from 3 to 8 carbon atoms, or from 3 to 5 carbon atoms. The gas precursor can be a perfluoroethane, perfluoropropane, perfluorobutane, or perfluoropentane. In addition, the gas precursor can be a sulfur containing fluorinated or perfluorinated compound (i.e. sulfur hexafluoride). The gas precursor can be a hydrocarbon, for example a linear or branched hydrocarbon having from 2 to 10 carbon atoms, from 3 to 10 carbon atoms, from 3 to 8 carbon atoms, or from 3 to 5 carbon atoms. The gas precursor can be a hydrofluorocarbon containing one or more hydrogen atoms or other substituents in place of the fluorine. The hydrofluorocarbon can have from 2 to 10 carbon atoms, from 3 to 10 carbon atoms, from 3 to 8 carbon atoms, or from 3 to 5 carbon atoms. The gas precursor can also contain other halofluorocarbon such as those containing chlorine or bromine. The halofluorocarbon can have from 2 to 10 carbon atoms, from 3 to 10 carbon atoms, from 3 to 8 carbon atoms, or from 3 to 5 carbon atoms. The gas precursor can be a mixture of fluorocarbons, hydrocarbons, hydrofluorocarbons, and/or halofluorocarbons.

The LBLnNDs contain phase change nanodroplets which can be encased in an outer shell such as lipid monolayer or a lipid bilayer and can be unilamellar or multilamellar. The shell can contain one or more different lipids. For example, the outer shell can contain a neutral lipid, a cationic lipid, an anionic lipid, or a combination thereof. Suitable lipids can include, for example, sterols and lipids such as sterols, cholesterol, phospholipids, lysolipids, lysophospholipids, sphingolipids, ceramides, or pegylated lipids.

Nanodroplets are known in the art. The nanodroplet and/or nanodroplet membrane can be lipid micelles, liposomes, or solid lipid particles. The nanodroplet can be made from one or a mixture of different lipids. Nanodroplets can be formed from one or more lipids, which can be neutral, anionic, or cationic at physiologic pH. The nanodroplet is preferably made from one or more biocompatible lipids. The nanodroplet may be formed from a combination of more than one lipid, for example, a charged lipid may be combined with a lipid that is non-ionic or uncharged at physiological pH.

The nanodroplet can be a lipid micelle. Lipid micelles for drug delivery are known in the art. Lipid micelles can be formed, for instance, as a water-in-oil emulsion with a lipid surfactant. An emulsion is a blend of two immiscible phases wherein a surfactant is added to stabilize the dispersed droplets. In some embodiments the lipid micelle is a microemulsion. A microemulsion is a thermodynamically stable system composed of at least water, oil and a lipid surfactant producing a transparent and thermodynamically stable system whose droplet size is less than 1 micron, from about 10 nm to about 500 nm, or from about 10 nm to about 250 nm. Lipid micelles are generally useful for encapsulating hydrophobic active agents, including hydrophobic therapeutic agents, hydrophobic prophylactic agents, or hydrophobic diagnostic agents.

The nanodroplet can be a liposome. Liposomes are small vesicles composed of an aqueous medium surrounded by lipids arranged in spherical bilayers. Liposomes can be classified as small unilamellar vesicles, large unilamellar vesicles, or small or large multi-lamellar vesicles. Multilamellar liposomes contain multiple concentric lipid bilayers. Liposomes can be used to encapsulate agents, by trapping hydrophilic agents in the aqueous interior or between bilayers, or by trapping hydrophobic agents within the bilayer.

The lipid micelles and liposomes can have an aqueous center. The aqueous center can contain water or a mixture of water and alcohol. Suitable alcohols include, but are not limited to, methanol, ethanol, propanol, (such as isopropanol), butanol (such as n-butanol, isobutanol, sec-butanol, tert-butanol, pentanol (such as amyl alcohol, isobutyl carbinol), hexanol (such as 1-hexanol, 2-hexanol, 3-hexanol), heptanol (such as 1-heptanol, 2-heptanol, 3-heptanol and 4-heptanol) or octanol (such as 1-octanol) or a combination thereof. The aqueous center can also contain buffers or even DMSO or DMF.

The nanodroplets can be a solid lipid particle. Solid lipid particles present an alternative to the colloidal micelles and liposomes. Solid lipid particles are typically submicron in size, i.e. from about 10 nm to about 1 micron, from 10 nm to about 500 nm, or from 10 nm to about 250 nm. Solid lipid particles are formed of lipids that are solids at room temperature. They are derived from oil-in-water emulsions, by replacing the liquid oil by a solid lipid.

Suitable neutral and anionic lipids include, but are not limited to, sterols and lipids such as cholesterol, phospholipids, lysolipids, lysophospholipids, sphingolipids or pegylated lipids, saturated or unsaturated acyl lipids. Neutral and anionic lipids include, but are not limited to, phosphatidyl-choline (PC) (such as egg PC, soy PC), including 1,2-diacyl-sn-glycero-3-phosphocholines; phosphatidylserine (PS), phosphatidylglycerol, phosphatidylinositol (PI); glycolip-ids; sphingophospholipids such as sphingomyelin and sphin-goglycolipids (also known as 1-ceramidyl glucosides) such as ceramide galactopyranoside, gangliosides and cerebro-sides; fatty acids, sterols, containing a carboxylic acid group for example, cholesterol; 1,2-diacyl-sn-glycero-3-phospho-ethanolamine, including, but not limited to, 1,2-dioleylphos-phoethanolamine (DOPE), 1,2-dihexadecylphosphoetha-nolamine (DHPE), 1,2-distearoylphosphatidylcholine (DSPC), 1,2-dipalmitoyl phosphatidylcholine (DPPC), and 1,2-dimyristoylphosphatidylcholine (DMPC). The lipids can also include various natural (e.g., tissue derived L-$\alpha$-phos-phatidyl: egg yolk, heart, brain, liver, soybean) and/or syn-thetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of the lipids.

Suitable cationic lipids include, but are not limited to, N-[1-(2,3-dioleoyloxy)propyl]-N,N,N-trimethyl ammonium salts, also references as TAP lipids, for example methylsul-fate salt. Suitable TAP lipids include, but are not limited to, DOTAP (dioleoyl-), DMTAP (dimyristoyl-), DPTAP (di-palmitoyl-), and DSTAP (distearoyl-). Suitable cationic lip-ids in the liposomes include, but are not limited to, dimeth-yldioctadecyl ammonium bromide (DDAB), 1,2-diacyloxy-3-trimethylammonium propanes, N-[1-(2,3-dioloyloxy) propyl]-N,N-dimethyl amine (DODAP), 1,2-diacyloxy-3-dimethylammonium propanes, N-[1-(2,3-dioleyloxy) propyl]-N,N,N-trimethylammonium chloride (DOTMA), 1,2-dialkyloxy-3-dimethylammonium propanes, diocta-decylamidoglycylspermine (DOGS), 3-[N—(N',N'-dimeth-ylamino-ethane)carbamoyl]cholesterol (DC-Chol); 2,3-dio-leoyloxy-N-(2-(sperminecarboxamido)-ethyl)-N,N-dimethyl-1-propanaminium trifluoro-acetate (DOSPA), 6-alanyl cholesterol, cetyl trimethyl ammonium bromide (CTAB), N-tert-butyl-N'-tetradecyl-3-tetradecylamino-pro-pionamidine, N-(alpha-trimethylammonioacetyl)didodecyl-D-glutamate chloride (TMAG), ditetradecanoyl-N-(trimeth-ylammonio-acetyl)diethanolamine chloride, 1,3-dioleoyloxy-2-(6-carboxy-spermyl)-propylamide (DOSPER), and N, N, N', N'-tetramethyl-, N'-bis(2-hy-droxylethyl)-2,3-dioleoyloxy-1,4-butanediammonium iodide. In one embodiment, the cationic lipids can be 1-[2-(acyloxy)ethyl]2-alkyl(alkenyl)-3-(2-hydroxyethyl)-imidazolinium chloride derivatives, for example, 1-[2-(9(Z)-octadecenoyloxy)ethyl]-2-(8(Z)-heptadecenyl-3-(2-hy-droxyethyl)imidazolinium chloride (DOTIM), and 1-[2-(hexadecanoyloxy)ethyl]-2-pentadecyl-3-(2-hydroxyethyl) imidazolinium chloride (DPTIM). In one embodiment, the cationic lipids can be 2,3-dialkyloxypropyl quaternary ammonium compound derivatives containing a hydroxyal-kyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-di-methyl-hydroxypropyl ammonium bromide (DORIE-HP), 1,2-dioleyl-oxy-propyl-3-dimethyl-hydroxybutyl ammo-nium bromide (DORIE-HB), 1,2-dioleyloxypropyl-3-dim-ethyl-hydroxypentyl ammonium bromide (DORIE-Hpe), 1,2-dimyristyloxypropyl-3-dimethyl-hydroxylethyl ammo-nium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

Suitable solid lipids include, but are not limited to, higher saturated alcohols, higher fatty acids, sphingolipids, syn-thetic esters, and mono-, di-, and triglycerides of higher saturated fatty acids. Solid lipids can include aliphatic alcohols having 10-40, preferably 12-30 carbon atoms, such as cetostearyl alcohol. Solid lipids can include higher fatty acids of 10-40, preferably 12-30 carbon atoms, such as stearic acid, palmitic acid, decanoic acid, and behenic acid. Solid lipids can include glycerides, including monoglycer-ides, diglycerides, and triglycerides, of higher saturated fatty acids having 10-40, preferably 12-30 carbon atoms, such as glyceryl monostearate, glycerol behenate, glycerol palmito-stearate, glycerol trilaurate, triacetin, tricaprin, trilaurin, trimyristin, tripalmitin, tristearin, and hydrogenated castor oil. Suitable solid lipids can include cetyl palmitate, bees-wax, or cyclodextrin.

The LBLnNDs can be a hybrid particle. Hybrid particle, as used herein, refers to a particle that combines the features of two or more of polymeric particles, lipid particles, and inorganic particles. Examples of hybrid particles can include polymer-stabilized liposomes, polymer-coated inorganic particles, or lipid-coated polymeric particles. The hybrid particle can contain a polymeric inner region, a lipid inner region, or an inorganic inner region. The hybrid particle can contain a polymer outer layer, a lipid outer layer, or an inorganic outer layer.

The LBLnNDs can be a polymer-stabilized lipid particle, such as a polymer-stabilized liposome. Polymer-stabilized liposomes are described, for example, in WO 2008/082721 by Dominguez et al. The LBLnNDs can be a polymer-stabilized solid lipid particle. Solid lipid particles have been coated with polymers to impart stability (see Nahire et al., Biomacromolecules 14:841-853 (2013)) or to impart stealth properties (see Uner and Yener, Int. J. Nanomedicine 2:289-300 (2007)). The polymer-stabilized liposomes and poly-mer-stabilized solid lipid particles include a lipid particle stabilized by the presence of a coating polymer. The coating polymer can be covalently or non-covalently bound to the lipid particle. The coating polymer can be a lipophilic polymer, a biodegradable polymer, a stealth polymer, or a combination thereof.

The LBLnNDs can be a polymer-stabilized inorganic particle such as a polymer-coated metal nanoparticle. WO 2013/070653 by Alocilja et al. described metal nanoparticle stabilized by a polysaccharide coating polymer.

Suitable lipophilic polymers can include aliphatic poly-esters, such as polylactic acid, polyglycolic acid and their copolymers; poly($\varepsilon$-caprolactone), poly($\delta$-valerolactone), polyesters with longer (i.e., Ci5 to C25) hydrocarbon chains; dendritic polymers of polyesters containing a modified ter-minal hydroxyl; aliphatic and aromatic polycarbonates; ali-phatic polyamides, polypeptides; polyesteramides; polyure-thanes; silicones, such as poly(dimethylsyloxanes); lipophilic poly(phosphazenes); poly(methacrylic acid), poly (styrene) and hydrophobic polyacrylic, polyvinyl and poly-styrene carriers.

Suitable stealth polymers can include homo polymers or copolymers of polyalkene glycols, such as poly(ethylene glycol), poly(propylene glycol), poly(butylene glycol), and may include acrylates and acrylamide, such as hydroxyethyl methacrylate and hydroxypropylmethacrylamide respec-tively.

Suitable biodegradable polymers can include polyamides, polycarbonates, saturated polyalkyls, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly (isobutylmethacrylate), poly(hexylmethacrylate), poly(isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene and polyvinylpyrrolidone, derivatives thereof, linear and branched copolymers and block copolymers thereof, and blends thereof. Exemplary biodegradable polymers include polyesters, poly(ortho esters), poly(ethylene imines), poly(caprolactones), poly(hydroxybutyrates), poly(hydroxyvalerates), polyanhydrides, poly(acrylic acids), polyglycolides, poly(urethanes), polycarbonates, polyphosphate esters, polyphosphazenes, derivatives thereof, linear and branched copolymers and block copolymers thereof, and blends thereof. In particularly preferred embodiments the polymeric core contains biodegradable polyesters or polyanhydrides such as poly(lactic acid), poly(glycolic acid), and poly(lactic-co-glycolic acid).

The LBLnNDs can contain an active agent that has a therapeutic, prophylactic, diagnostic, and/or imaginal effect. Any therapeutic, prophylactic, diagnostic or imaginal agent can be encapsulated in the LBLnNDs. Suitable agents include, but are not limited to, the agents listed below. In some embodiments the LBLnNDs have a therapeutic, prophylactic, diagnostic, or imaginal effect.

The loading range for the agent within the LBLnNDs is from about 0.01 to about 80% (agent weight/nanoparticle weight), from 0.01% to about 50% (wt/wt), from about 0.01% to about 25% (wt/wt), from about 0.01% to about 10% (wt/wt), or from about 0.1% to about 5% (wt/wt). For small molecules, the percent loading can be from about 0.01% to about 20% (wt/wt), although higher loadings may be achieved for nanoparticles containing agent alone without polymer, lipid, etc. and/or for hydrophobic drugs and/or insoluble agents.

For large biomolecules, such as proteins and nucleic acids, typical loadings are from about 0.01% to about 5% (wt/wt), from about 0.01% to about 2.5% (wt/wt), or from about 0.01% to about 1% (wt/wt). The loading can be calculated relative to the mass of the LBLnNDs.

The active agent can be a protein or peptide, small molecule, nucleic acid or nucleic acid molecule, lipid, sugar, glycolipid, glycoprotein, lipoprotein, or combination thereof. In some embodiments, the active agent is an antigen or adjuvant, radioactive or imaging agent (e.g., a fluorescent moiety) or polynucleotide. In some embodiments the active agent is an organometallic compound.

Active agents include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics. Active agents can include antibodies and biological products such as such as Herceptin and other MAbs.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammatories (e.g. ibuprofen, naproxen, ketoprofen, and other non-steroidal anti-inflammatories commonly referred to as NSAIDs to one skilled in the art, and nimesulide), aspirin and related salicylates (e.g. choline salicylate, magnesium salicylate, and sodium salicylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbituates, hyxdroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylae, and sodium salicaylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g. nitazoxanide, paromomycin, metronidazole, tinidazole, chloroquine, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethanmbutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/ tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxacillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, aspargainase erwinia chyrsanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

Methods of Making LBLnNDs

Methods of making nanodroplets/nanoparticles are well known in the art. The layer-by-layer approach to modify nanodroplets/nanoparticles is also known in the art. The present disclosure provides alternating charged biopolymers layer-by-layer (LBL) onto the surface of the nanodroplets.

The modified LBLnNDs are then verified via zeta potential analysis and size distribution measure. Exemplary methods of making the LBLnNDs of the present disclosure are provided in detail in Examples below.

In addition, the size distribution upon addition of layers appears to be less polydisperse, possibly a result of charge-charge repulsion thereby discouraging aggregation and coalescence. The particle size appeared to trend towards smaller diameter; possibly a reflection of increased electro-static interaction; and increasing the number of layers mar-ginally increases the effective diameter. While this decrease in size could be a result of how the Malvern Zetasizer measures relative diameter, the size reduction could also be a result electrostatic interaction stabilizing the membrane, reducing the diameter and thereby increasing stability via greater Laplace pressures.

Methods of Using LBLnNDs

The use of alternating charges in a layer-by-layer (LBL) assembly format can offer advantages with respect to drug and gene delivery. For example, should the terminal outside layer be comprised of poly-lysine (L- or D-), the nanodroplet can be used as a carrier for plasmids for the purposes of gene-delivery. Alternatively, the negatively charged layer may offer "handles" for conjugating targeting ligands, fluo-rescent labels, and/or drugs for more efficient drug delivery.

In addition, should this technology be applicable to con-densation/stabilization of even more volatile gaseous cores (i.e. octafluoropropane, −37° C.), the additional stability could offer added clinical application. For example, Choud-hary and coworkers (*PLoS One.,* 13(12):e0207486, 2018) were recently able to transiently image the myocardial infarct zone in both rats and pigs utilizing condensed Defin-ity (octafluoropropane) microbubbles using a Siemens ultra-sound platform and frequency of 1.3-2 MHz and a mechani-cal index on the order of 1.3-1.5 respectively. The perfluoropropane PCCAs were activated using FDA approved mechanical indices which probably could not be achieved using perfluorobutane PCCAs. As such, the present disclosure suggests that perfluoropropane LBL PCCAs could offer similar or even superior myocardial scar imaging yet with pulse sequences that could satisfy FDA approved mechanical indices.

In certain embodiments, the present disclosure provides a layer-by-layer assembly approach to coat the membrane PCCA's enhances the particles thermal stability while not affecting the acoustic stability of the PCCA. Successful application of up to 20 layers (10 sets) of alternating positively and negatively charged biopolymers onto the surface membrane of decafluorobutane gas-condensed nano-droplets (DFB-NDs) was demonstrated. The thermal and acoustic properties of DFB-ND's layered with 6 and 10 sets of charge alternating biopolymers (LBL$_6$-ND's and LBL$_{10}$-ND's) were studied and compared to the corresponding non-layered DFB-ND's. Results indicated that the layered PCCAs had higher thermal stability; where the half-life of the LBL$_x$-NDs at both 37° C. and 45° C. was significantly increased.

Furthermore, acoustic vaporization profiles as a function of mechanical index were generated for the DFB-NDs, LBL$_6$-NDs, and LBL$_{10}$-NDs. Results indicated that there is no significant difference between the acoustic vaporization profiles of non-layered control vs. the layered nanodroplets. Thus, the results presented substantiate two major claims; first, biopolymeric layering of DFB-NDs imparts a thermal stabilizing effect. Interestingly, the increased thermal stabil-ity does not appear to be correlated with an increase in number of layers added suggesting there may be a finite number of layers that will impart the thermal stability effect. Secondly, both LBL$_6$-NDs and LBL$_{10}$-NDs did not appear to alter particle acoustic vaporization thresholds, suggesting that the thermal stability of the particle may not necessarily be coupled with the acoustic vaporization thresholds.

Phase-change contrast agents represent a nanodroplet-based moiety that offers advantages over traditional microbubbles as CEUS agents. Their small size and increased circulation lifetimes can offer alternative uses to bubble-based technology. However, PCCAs with previously reported lipid shells become more labile as the perfluoro-carbon used becomes more volatile (i.e., lower boiling point). The present disclosure provides stabilized the nano-droplets using a layer-by-layer assembly approach to modify the membrane. The nanodroplets disclosed in the present disclosure have revealed interesting results that have sig-nificant implications for clinical translation.

In certain embodiments, the present disclosure provides studies concerning lipid PFC-PCCAs, suggesting that uti-lizing higher boiling perfluorocarbon gasses, increases both the thermal and acoustic stability of the PFC-PCCA; here, acoustic stability refers to the ADV threshold. The results presented in the present disclosure indicate that there is a possibility to uncouple thermal and acoustic stability with an LBL membrane approach. Furthermore, the present disclo-sure also provides that the droplet half-life and the sponta-neous thermal vaporization thresholds increases when DFB-ND's are layered with charge alternating biopolymers, however, it is noted that an increase in the number of layers may not necessarily correlate with increased thermal stabil-ity.

In addition, the LBL layering may have an effect on the size distribution of the droplets tending toward a less polydisperse emulsion. This phenomenon could be possible because of charge-charge repulsion of the outermost layer whereby aggregation and coalescence are discouraged. The droplet size appeared to trend towards smaller diameters; possibly a reflection of increased electrostatic interactions between successive polyelectrolyte layers thereby decreas-ing the relative volumetric size of the droplet.

Increasing the number of layers would marginally increase the effective diameter, but from the data presented herein it is noted that a possible mechanism for the observed phenomena is an increase PFC core Laplace pressure. It is unknown whether the entire volume of decafluorobutane—PFC gas trapped inside the liposomal cavity prior to con-densation experiences a phase transition to a liquid state. Furthermore, the trapped decafluorobutane exists at or near its critical point, thus advancing the possibility of phase coexistence between liquid and gaseous decafluorobutane. This phenomenon is important when coupled with the deposition of polyelectrolytic films. The electrostatic inter-actions occurring between the lipid core and polyelectro-lytes, contraction of the DFB-ND core; where this would only be possible if decafluorobutane was a compressible fluid, which it is not, or if the trapped decafluorobutane featured phase coexistence. If this were not the case, an increase in droplet size upon the deposition of the polyelec-trolytes would likely be observed, as shown in the LBL liposomal literature. The decrease in size could be an artifact of the DLS technique implemented from the Malvern Zeta-sizer, however, in the studies disclosed herein each sample was measured (N=11) with good agreement in particle size for each layered set, indicating that the present disclosure is in-line with the noted results.

The use of alternating charges in a layer-by-layer assem-bly format can offer advantages with respect to drug and gene delivery. For example, should the terminal outside layer comprise poly-lysine (L- or D-), the droplet can be used as a carrier for plasmids for the purposes of gene delivery. Alternatively, the negatively charged outermost layer may offer "handles" for conjugating targeting ligands, fluorescent labels, or drugs for more efficient drug delivery.

In certain studies, the data indicate that $LBL_{10}$-NDs do not appear to further stabilize the droplets at 45° C., and in fact, the half-life appears similar to, or even less, than the corresponding $LBL_6$-NDs at the same temperature (see Table 1). However, the DFB-ND core present in all samples is composed predominantly of DPPC which has a phase transition temperature of 41° C.; where cooler temperatures form a gel phase while warmer temperatures adopt a liquid-crystalline state. The data are consistent with the increased number of layers benefitting from the stability of a gel phase however not so with a liquid-crystalline phase. Furthermore, the fluid state membrane does not provide a stable template to support increasingly thicker LBL deposition, so the ND collapses more readily under the weight of $LBL_{10}$-ND. This could result in lower stability as determined by the smaller number of droplets activated with time. Regardless of the phenomenon occurring at temperatures above 41° C., the stability of the gel phase is considerably greater than the liquid-crystalline phase and that the more relevant temperatures, <41° C. common in mammalian systems should be focused on, whereas, >41° C. stability may be of marginal interest.

Furthermore, while six (6) sets of layers increased the half-life of the DFB-NDs, additional sets of layers may offer greater stability, using the present method. However, the increasing stability offered by increasing electrostatic interactions (more layers=more charges) is eventually offset by the loss of colloidal stability (more layers=more polymers; all denser than water). Clearly, modifications to the LBL assembly (i.e. shorter or longer polymer length/greater of less charge-to-polymer ratios) could provide greater insight into the ability to stabilize the NDs.

Moreover, should the technology presented in the present disclosure be applied to condensation/stabilization of even more volatile gaseous cores (i.e., octafluoropropane (OFP), −37° C.), the additional stability may offer added clinical application. For example, Choudhury and coworkers were recently able to transiently image the myocardial infarct scar zone in both rats and pigs using Definity OFP-NDs and Siemens ultrasound platform with frequencies of 1.3-2 MHz and activation mechanical index on the order of 1.3-1.5 respectively. The OFP-NDs were activated using FDA-approved MI's, which probably could not be achieved efficiently using DFB-ND's. As such, the OFP-LBL-ND's could offer similar myocardial scar imaging yet with pulse sequences that will satisfy FDA-approved mechanical indices. The susceptibility of OFP-ND's to ultrasound activation could be critical as tissue attenuation of ultrasound does increase mechanical index requirements for activation, thereby making the utility of higher boiling perfluorocarbons condensed in the core somewhat of a limitation.

Research concerning the thermal and acoustic stability of volatile PFC-PCCA nanodroplets focuses on alterations to either the perfluorocarbon core or the surface membrane design. It is well established that the thermal and acoustic stability of a PCCA is dependent on the volatility of the perfluorocarbon core; where low volatility PFCs offer increased thermal stability as well as increased acoustic phase transition energy requirements relative to high volatility PFCs. Furthermore, recent studies have shown that utilizing PFC mixtures may allow for tunability of both thermal and acoustic properties. However, studies have not directly assessed thermal or acoustic tunability independent of one another. Concerning surface membrane modifications, several studies have made modifications via the incorporation of fluorocarbons, hydrocarbons, polymeric shell, polymeric crosslinked shells claiming to increase nanoparticle stability. Similarly, studies have not directly assessed thermal or acoustic tunability where an emphasis has been placed on particle size and zeta-potential as a measure of stability. The present disclosure provides studies that assess the acoustic and thermal properties of volatile perfluorocarbons with an LBL surface modification approach. The results presented herein indicate that layer-by-layer assemblies allow for the modulation of the PCCA's thermal stability whilst not affecting the acoustic phase transition threshold (i.e. not increasing the MI necessary for acoustic activation).

Although more work needs to be done with respect to LBL stabilization, the present disclosure provides that PFC-PCCAs can be modified to thermally stabilize the droplets without compromising acoustic activation parameters to any significant extent. The layer-by-layer methodology of the present disclosure can be further used to evaluate whether tighter control of thermal vs. acoustic activation can be exploited to incorporate PFC-PCCAs in novel applications.

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Materials and Methods

Nanodroplet Formulation and Characterization
Formulation Materials

Methoxy-polyethylene-glycol-block-poly-L-aspartic-acid-sodium-salt (mPEG-b-PLD, MW: 12,000) was obtained from Alamanda Polymers (Huntsville, AL, USA). The block lengths were 113 and 50 repeating units for PEG and PLD, respectively. Poly-L-lysine solution (PLL, MW: 150,000-300,000, 0.1% (w/v)) was purchased from Sigma-Aldrich (St Louis, MO, USA). 1,2-Dipalmitoyl-sn-glycero-3-phosphocholine (DPPC), 1,2-dipalmitoyl-sn-glycero-3-phosphatidylethanolamine-polyethyleneglycol-2000 (DPPE-PEG-2000), and 1,2-dipalmitoyl-3-trimethylammonium propane (chloride salt; 16:0 TAP) were obtained from (Avanti Polar Lipids, Alabaster, AL). Decafluorobutane (99.8% purity) was purchased from Fluoromed (Round Rock, TX).

Formulation of Microbubbles

A lipid mixture comprising 1,2-dipalmitoyl-sn-glycero-3-phosphocholine (DPPC), 1,2-dipalmitoyl-sn-glycero-3-phosphatidylethanolamine-polyethyleneglycol-2000 (DPPE-PEG-2000), and 1,2-dipalmitoyl-3-trimethylammonium propane (chloride salt; 16:0 TAP) in a molar ratio of 65:5:30 and a total lipid concentration of 0.50 mg/m, was dispersed in an excipient liquid consisting of propylene glycol, glycerol, and normal saline (15:5:80, v:v:v). A 1.5 mL aliquot was then added to a 2 mL vial (Wheaton Industries, Wheaton, MA), covered with a rubber septum cap and sealed with an aluminum crimp. The headspace of the vial was then degassed on a vacuum manifold followed by purging with decafluorobutane. Samples were then agitated at 4500 rpm for 45 seconds using a modified dental amalgamator (Lantheus, New York, NY) to yield microbubbles (approx. $1-5\times10^9$ microbubbles $mL^{-1}$).

Formulation of DFB-NDs Via Condensation

The resulting microbubbles were then cooled in an ice/salt bath to $-5°$ C.$--8°$ C. and pressurized with ambient air by puncturing the vial septum with an 18 G needle connected to a 60 mL plastic syringe. Approximately 60 cc of air was forced into the vial (approx. 750 kPa, 85-110 psi). Upon addition of air, the creamy white foam (MBs) turned opaque (NDs); an indication that successful condensation had occurred as smaller particles have a reduced light scattering effect. The syringe needle was removed from the vial after pressurizing, leaving a pressure head on the NDs.

Formulation of $LBL_x$-NDs $LBL_x$-NDs were generated in a similar fashion as reported by Ramasamy and coworkers for liposomes [Ramasamy et al 2014]. Briefly, a 6 mg/mL aliquot of mPEG-b-PLD was prepared (in $H_2O$). A 33 μL aliquot was added to the DFB-ND dispersion and vortexed for 90 seconds using a VWR Analog Mini-Vortex Mixer set to Level 3 (Model 58816-121, 3200 rpm speed, VWR, Aurora, CO). Thereafter, 200 μL of the 0.1% (w/v) PLL was added to the mPEG-b-PLD layered DFB-ND dispersion and vortexed for an additional 90 seconds on Level 3 setting (RPM). Addition of subsequent layers consisted of alternating the addition of 18 μl of PEG-b-PLD aliquot and 100 μL 0.1% (w/v) PLL until 3 sets of layers ($LBL_6$-ND) and 5 sets ($LBL_{10}$-ND) were accomplished. Sizing and zeta potential measurements were conducted after each layering process.

Nanodroplet Sizing

Nanodroplet sample size distributions were measured using a Malvern Nano ZS (Malvern Instruments Ltd., Malvern, Worcestershire, U.K.). The Malvern Nano ZS is capable of measuring particles as small as 1 nm in diameter. Approximately 100 μL of condensed droplet/LBL-NDs were transferred via micropipette to a cuvette with 1.4 mL of nano-pure water (pH=7).

Characterization of Layer by Layer Deposition

Alternate deposition of polymers mPEG-b-PLD and PLL onto the surface of the DFB-ND, composed of DPPC-TAPS-PEG-2k, was verified via zeta potential analysis using a Malvern Nano ZS. A 50 μL aliquot of condensed LBL droplets was transferred via micropipette to a disposable zeta-cuvette (Part No. DTS1070, Malvern Instruments Ltd., Malvern, Worcestershire, U.K.) along with 0.750 mL of nano-pure water (pH=7).

Nanodroplet Incubation

All nanodroplets (NDs) were incubated at 37° C. and 45° C. A Symphony, forced air incubator, Model 414004-588 (VWR Corp., Aurora, CO) was utilized for temperature control at 37° C. Concurrently, a Panasonic Cell-IQ Series 5.8 cu.ft. $CO_2$ Laboratory Incubator (Panasonic Healthcare Corp., Wood Dale, Il) was utilized for temperature control at 37° C.

Determining Acoustic Properties of Nanodroplets

Vaporization events and thresholds were determined using a Vantage64 LE open ultrasound platform (Verasonics Inc., Kirkland, WA) and a linear ultrasound array (L11-4) with center frequency of 7.24 MHz. Low amplitude plane waves producing 400 frames per second were used to detect the vaporization events within the imaging plane. A short, high amplitude activation pulse, varied within a clinical range for diagnostic imaging (MI<1.9), was focused into a chamber containing NDs to generate vaporization events. The pulse echo frames were then post-processed and analyzed via MATLAB. Activation events were detected by measuring frame-by-frame correlations. The number of activation events were quantified via image processing routines, where the signal-to-noise ratio was addressed, and individual particle vaporization events were quantified. Pressure from the ultrasound transducer was calibrated with an Onda HGL-200 hydrophone (Onda Corporation, Sunnyvale, CA).

Thermal Stability Studies

Incubation Parameters

After formulating DFB-NDs and $LBL_x$-NDs, samples were retained in the vial and vented to atmospheric conditions using a 18 G venting needle. Samples were then placed in an incubation chamber set at 37° C. and 45° C. respectively. Samples were then incubated for 24, 72, 96, 120, 144 hours (37° C.) and 12, 24, 36, 48, 72, 96 hours (45° C.).

Acoustic Stability Studies

A static window chamber with inner chamber dimensions of 10 mm×10 mm×30 mm (l:w:h) was constructed for either simultaneous or individual quantification of acoustic vaporization events in non-layered DFB-NDs and $LBL_x$-NDs. Samples were then evaluated for acoustic vaporization thresholds as a function of ultrasound output. Approximately 0.25 mL of DFB-NDs/$LBL_x$-NDs were transferred via micropipette to the window chamber containing 2.75 mL of nano-pure water. Samples were placed atop the center 32 elements of the ultrasound transducer (the L11-4 has a total of 128 elements) providing a 1 cm×3 cm field of view (FOV). The window chamber was sealed with Tegaderm™ and coupled to the transducer using ultrasound contact gel (Aerogel™).

Four ultrasound pulses were delivered at high pressures (at 20, 30, 35, 40, 50, 60, 65, 70, and 75V or at a corresponding MI of 0, 0.26, 0.55, 0.84 0, 94, 1.09, 1.36, 1.58, 1.75, 1.88, and 2.01) with a 1 second delay between each pulse. Note, low voltage plane wave imaging was conducted at 400 fps where 4 HIFU pulses occurred every 400 frames.

Videos of droplet phase transition during high pressure pulses were captured as MP4 files and analyzed in MATLAB using a peak detection threshold over background noise.

Statistical Analysis

Curve Fitting

Thermal Stability: Graphs of ultrasound-mediated droplet activation as a function of mechanical index (MI) generated at different time points (hours) were fitted to a sigmoidal curve utilizing the formula:

$$f(x) = \frac{a}{1 + e^{-b(x-c)}}$$

where a is the amplitude, b is the slope of the sigmoid curve, and c is the offset in the x-axis from the origin.

Half-Life: Graphs measuring ultrasound droplet activation as a function of time (thermal degradation) were fitted to a simple exponential curve:

$$f(x)=N_0e^{-\lambda x}$$

where $N_0$ is the amplitude, and $\lambda$ is the slope of the decay. All curves were fitted using a MATLAB (Mathworks, Natick MA) Curve Fitting Tool. The presented curve fittings were estimated via Non-Linear Least Squares Regression with 95% confidence.

Analysis of Covariance

Acoustic Stability: Graphs of ultrasound-mediated droplet activation as a function of mechanical index (MI) were fitted to a sigmoidal curve. The linear portions of the sigmoid were compared for closeness of fit via analysis of covariance to deduce the relationship between particle structure (layered/unlayered) and acoustic vaporization thresholds.

Analysis of covariance is widely used to compare two or more regression lines to each other; comparison of regression lines measure differences between either slope or intercept. Confidence values utilized for comparison: $\alpha=0.01$. All curves were fitted using MATLAB's native Statistics Toolbox.

Example 2

Nanodroplet Characterization

Figure 3A:
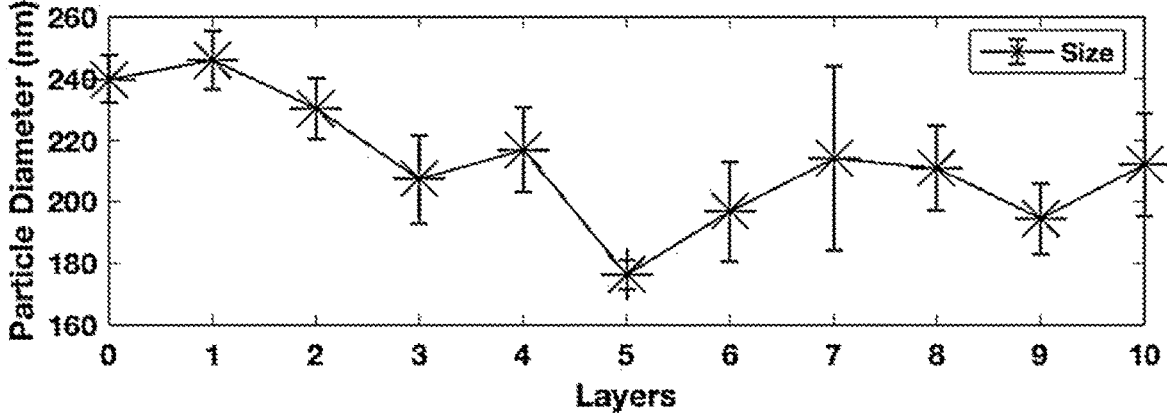
FIGS. 3A-3B. Droplet size and zeta potential.
Figure 3B:
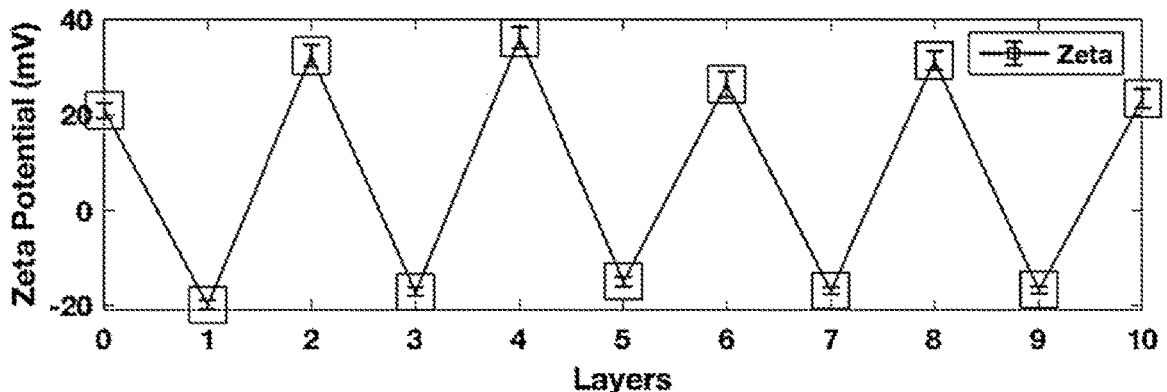
Figure 3C:
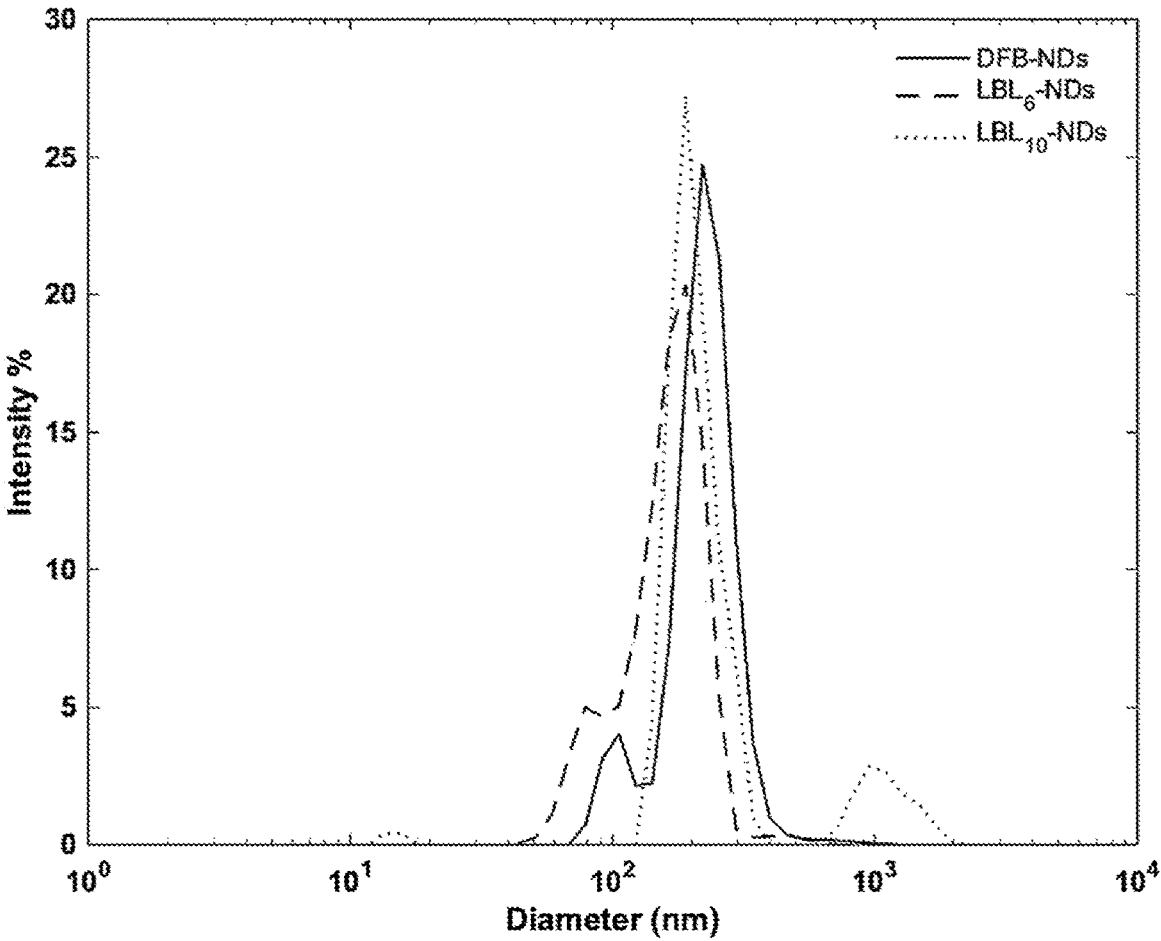
FIG. 3C. Graph of polydispersity of DFB-NDs, $LBL_6$-NDs, and $LBL_{10}$-NDs. All samples resulted in poly-disperse droplets showing peaks at 240.5 nm, 197.6 nm, 211.5 nm. Each curve is composed of N=11 samples.

Nanoparticle characterization was conducted via the Malvern Nano ZS measuring particle dynamic light scattering (DLS) and zeta potential, measurements were composed of N=11 samples for all three NDs. DLS exhibited a trend towards decreasing droplet size upon increasing the deposition of polyelectrolytes. The core, DFB-NDs, had a mean diameter of $240.5\pm22.9$ nm, the $LBL_6$-ND a diameter of $197.6\pm43.2$ nm, and the $LBL_{10}$-ND diameter measured $211.5\pm31.3$ nm (See FIGS. 3A-3C). It is worth noting that the unlayered (core) DFB-NDs exhibited the largest size and broadest distribution while the $LBL_6$-ND exhibited the smallest mean diameter. Note both the $LBL_6$-ND and $LBL_{10}$-ND appear to be less polydisperse than the DFB-NDs.

Zeta potential measurements demonstrated successful deposition of PEG-b-PLD onto the DFB-ND lipid membrane, PLL onto mPEG-b-PLD, and mPEG-b-PLD onto PLL. Alternation of the droplet's zeta potential upon the deposition of each polyelectrolyte is recursive.

Initial qualitative screening of $LBL_6$-NDs vs. control (non-layered DFB-NDs) were conducted in a 2-compartment chamber whereby samples were compared side-by-side using the same ultrasound pulse. The samples were incubated at 45° C. and at atmospheric pressure. After three days of incubation, qualitative and quantitative observations were noted. We could still clearly see the nanodroplet activation of $LBL_6$-NDs after a HIFU pulse vs. no activation with the DFB-NDs (no layering), an indication that the DFB-NDs had thermally degraded. In addition, we visually observed the formulations after the three day incubation period and noted the existence of a large number of gas bubbles in the DFB-ND emulsion in addition to much less opacification, an indication that the nanodroplets were thermally vaporized as any remaining perfluorocarbon nanodroplets would have the ability to induce more light dispersion (less clear) as opposed to the DFB-ND core (clearer formulation). These results thus motivated our characterization, thermal, and acoustic studies of $LBL_6$-NDs and $LBL_{10}$-NDs.

Example 3

Acoustic Stability Studies

Figures 4A, 4B, 5A, 5B, 5C:
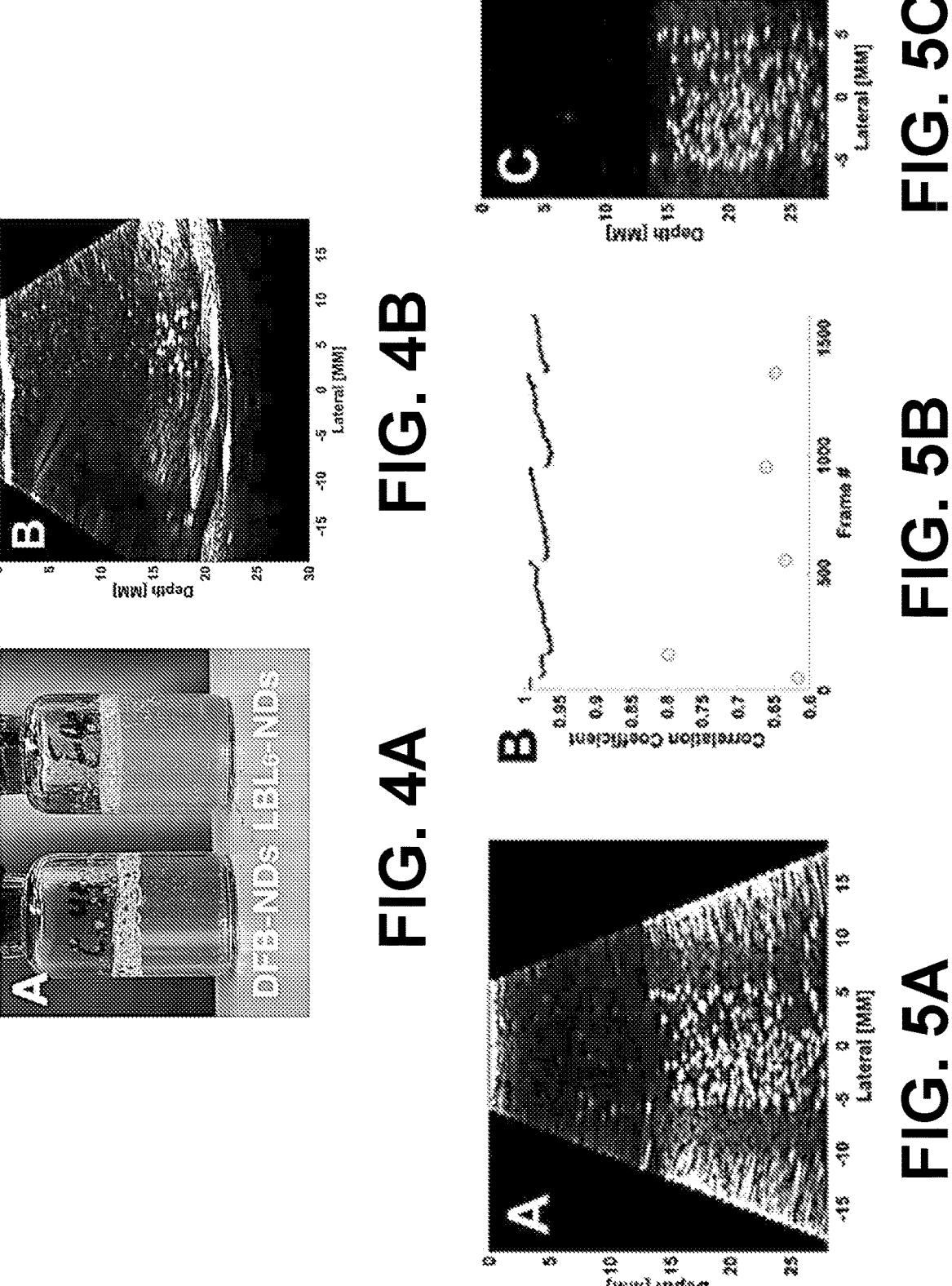
FIGS. 4A-4B. Comparison of DFB-NDs vs. $LBL_6$-NDs after three days incubation.
FIGS. 5A-5C. Demonstration of ND activation in a static chamber model.

Characterization of minimum acoustic pressure required for nanodroplet vaporization was quantified for DFB-NDs, $LBL_6$-NDs, and $LBL_{10}$-NDs. All emulsions were diluted 1:11 (v:v) with nano-pure water. Samples were then exposed to various acoustic pressures ranging from 0.27 to 2.01 MI. The data demonstrated that the minimum rarefaction pressure necessary for the activation of a droplet for both DFB-ND and $LBL_x$-ND was MI=0.84. Furthermore, by controlling the concentration of particles as well as the US transducer position and FOV, it was also possible to measure increased droplet vaporization as a function of peak rarefactional pressure. However, in order to do so, it was necessary to first differentiate between spontaneous vaporization caused by thermal functions in the chamber and mechanically induced vaporization via HIFU pulses. As such, we developed a program in MATLAB that could quantify new microbubbles in the first frame after ultrasound activation and subtract out those microbubbles (thermally vaporized) found in the frame immediately prior to the ultrasound pulse. The relative number of vaporized droplets as a function of MI for both DFB-NDs and $LBL_6$-NDs could then be fitted to a sigmoid curve (See FIGS. 5A-5C.).

Example 4

Thermal Stability Studies

Figures 6A, 6B:
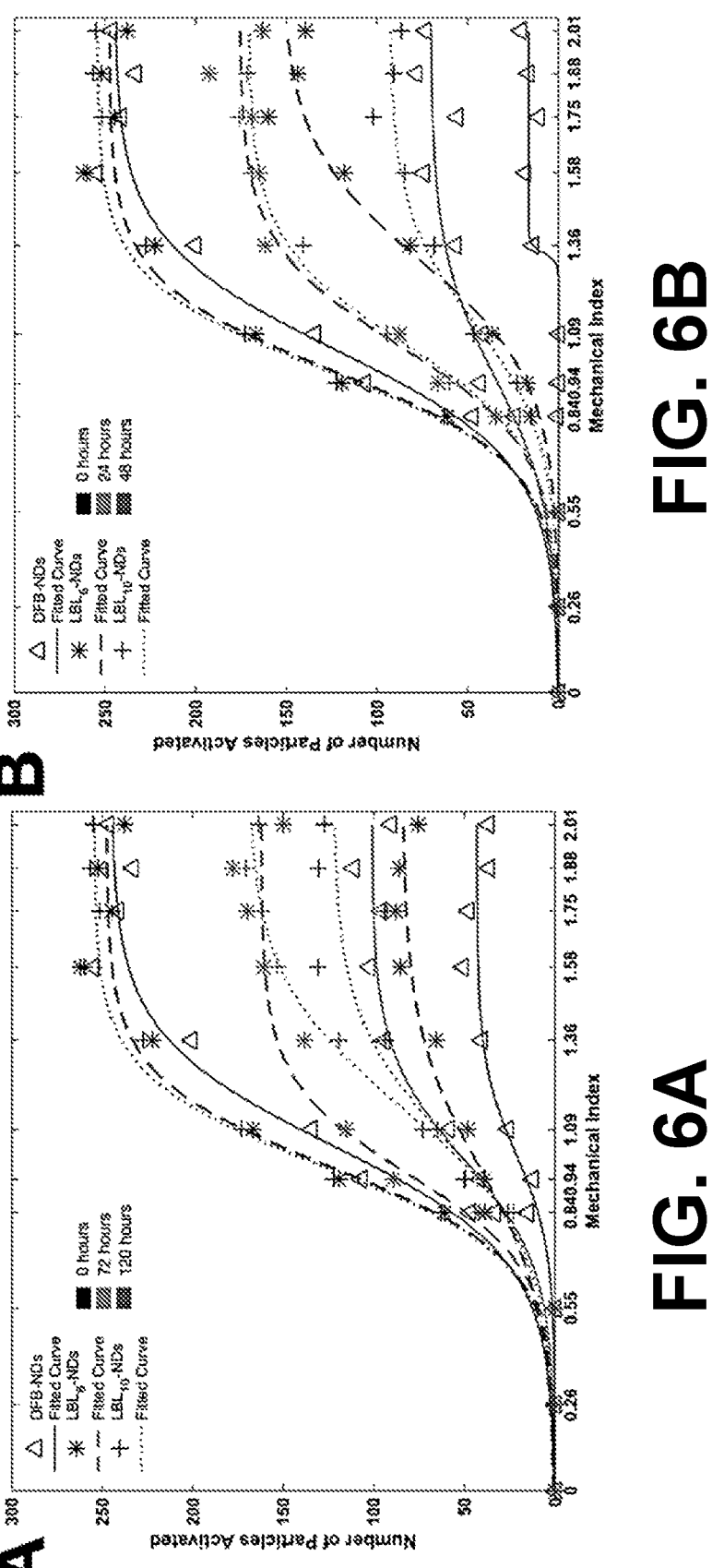
FIGS. 6A-6B. Graphs of Thermal Stability of DFB-NDs vs. $LBL_6$-ND and $LBL_{10}$-NDs at 37° C.
Figures 7A, 7B:
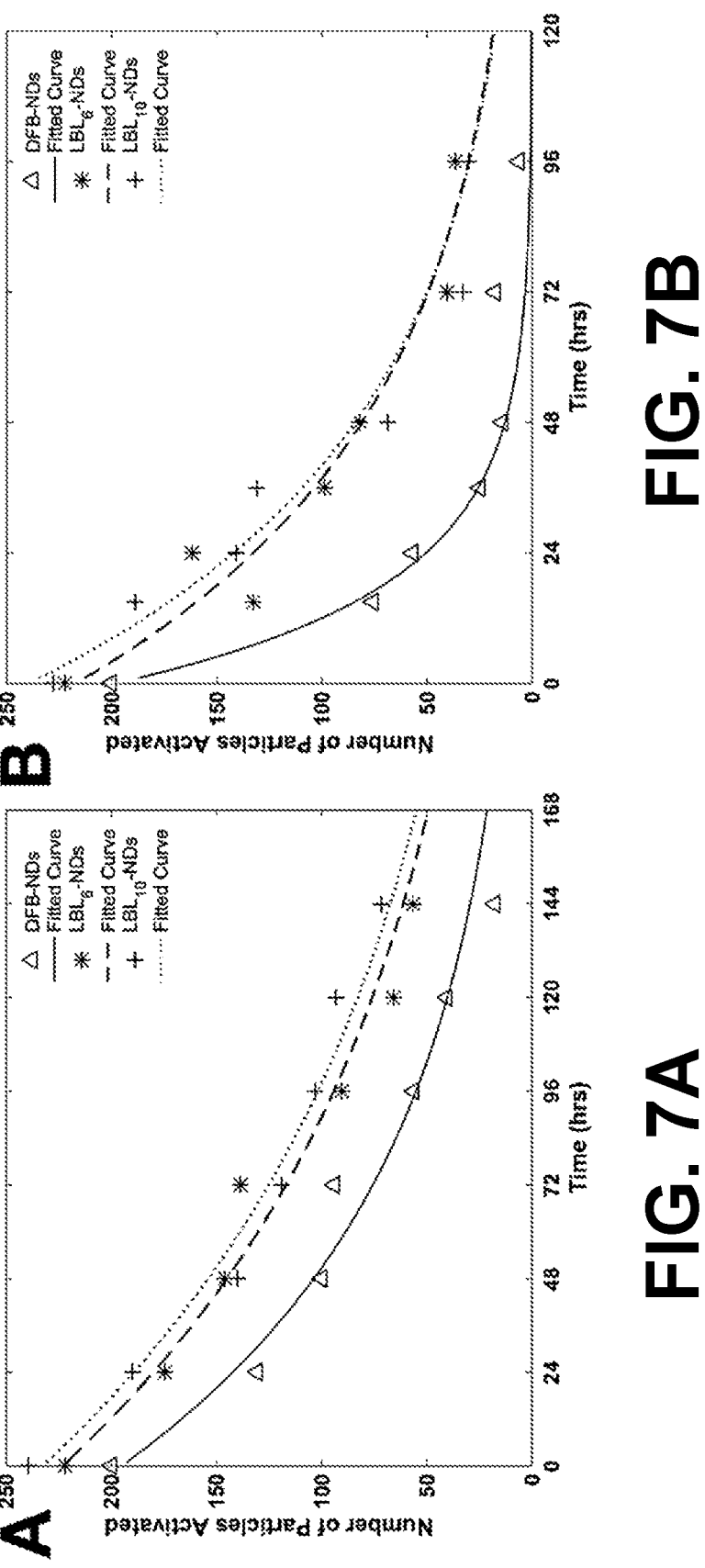
FIGS. 7A-7B. Graphs of half-life determinations for DFB-NDs (control) compared to $LBL_6$-NDs and $LBL_{10}$-NDs at 37° C.

Samples were studied utilizing the same methodology as that proposed to measure acoustic stability. All ND emulsions were diluted with nano-pure water by a factor of 1:11. Eight samples of each emulsion were subjected to thermal degradation studies where the peak rarefactional pressure that initiated droplet vaporization could be observed and number of vaporization events quantified. Furthermore, by controlling the concentration and FOV of the US transducer, it was also possible to map an increase in droplet vaporization as a function of an increase in peak rarefactional pressure. As is noted in FIGS. 6A-6B, the half-lives of both the $LBL_6$-NDs and $LBL_{10}$-NDs were greater than the control non-layered DFB-NDs at both (A) 37° C. and (B) 45° C. (Table 1). However, there is not a significant increase in half-life (stability) for the $LBL_{10}$-NDs relative to the $LBL_6$-NDs at 37° C. and a resultant decrease in stability for $LBL_{10}$-NDs vs. $LBL_6$-NDs at 45° C. (FIGS. 7A-7B).

TABLE 1

Half-life determinations for DFB-NDs (control) and $LBL_x$-NDs at 37° C. and 45° C. Fitted Exponential Decay curves quantified via MATLAB's curve fitting tool

| | 37° C. | | | 45° C. | | |
|---|---|---|---|---|---|---|
| Contrast Agent | Fitted Exponential *Decay* | $r^2$ Value | Half-Life (hrs.) | Fitted Exponential *Decay* | $r^2$ Value | Half-Life (hrs.) |
| DFB-NDs | $196.1e^{-0.0130t}$ | 0.9722 | 53.32 | $198.3e^{-0.0570t}$ | 0.9871 | 12.16 |
| $LBL_6$-NDs | $221.8e^{-0.0091t}$ | 0.9681 | 76.17 | $217.3e^{-0.0206t}$ | 0.9354 | 33.65 |
| $LBL_{10}$-NDs | $230.3e^{-0.0086t}$ | 0.9791 | 80.60 | $248.4e^{-0.0234t}$ | 0.9797 | 29.62 |

Example 5

Quantification of Acoustic Vaporization

Figures 8A, 8B:
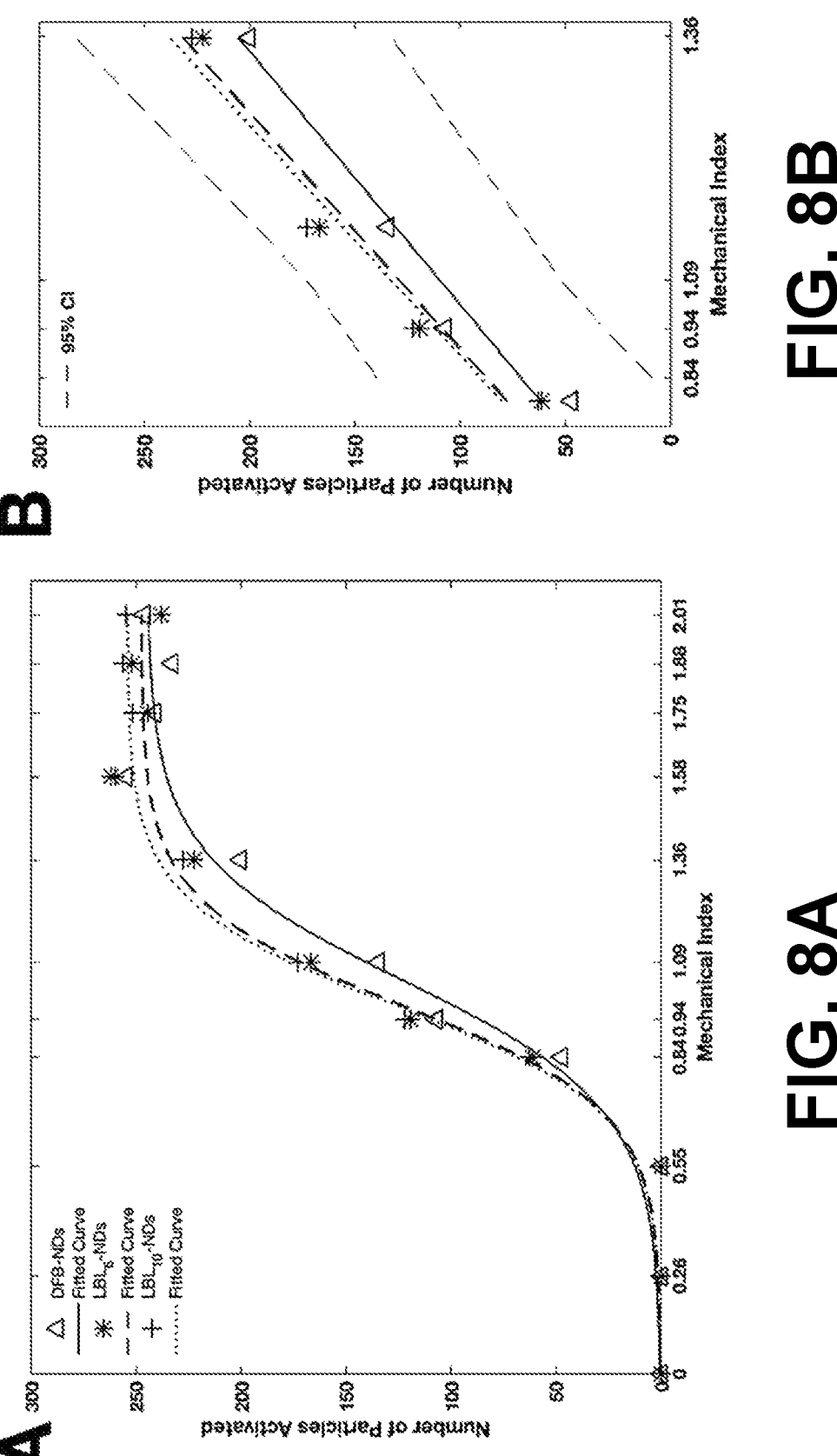
FIGS. 8A-8B. Quantification of Acoustic Vaporization (FIG. 8A) Thresholds (ND to MB transition) as a function of Mechanical Index. Quantification of vaporization thresholds performed immediately upon formulation (t=0).

All samples were then tested as to their acoustic vaporization. Once again, DFB-NDs, LBL$_6$-NDs, and LBL$_{10}$-NDs were tested for their ND to MB transition at 7.24 MHz and as a function of mechanical index. As shown in FIGS. 8A-8B, acoustic (N=8) thresholds were determined. It is noted that the linear portions of the curves corresponding to the MI range between 0.84 and 1.36 were examined for their slope. Linear regression determination showed the slopes to be very similar with R$^2$ values ranging from 0.9496 to 0.9920 (Table 2). Further analysis and comparison of the linear regression demonstrated that the 95% confidence intervals for the lower and upper limits for the true mean difference were no different when testing the hypothesis that the mean difference between the mean values was equal to zero (Table 3). P-values ranged between 0.8670 to 0.9894.

TABLE 2

Linear Regression determinations for DFB-NDs and LBL$_x$-NDs.
Fitted Linear Regressions quantified via MATLAB curve fitting tool

| Contrast Agent | Slope | R$^2$-value |
|---|---|---|
| DFB-NDs | 284.30 ± 30.51 | 0.9571 |
| LBL$_6$-NDs | 290.16 ± 28.96 | 0.9496 |
| LBL$_{10}$-NDs | 307.39 ± 33.53 | 0.9920 |

TABLE 3

Comparison of Linear Regressions between
DFB-NDs and LBL$_x$-NDs

| Variable 1 | Variable 2 | Lower Limit | $\mu_1 - \mu_2$ | Upper Limit | p-value |
|---|---|---|---|---|---|
| DFB-NDs | LBL$_6$-NDs | −132.92 | −5.86 | 121.19 | 0.9894 |
| DFB-NDs | LBL$_{10}$-NDs | −160.02 | −23.10 | 113.83 | 0.8670 |
| LBL$_6$-NDs | LBL$_{10}$-NDs | −151.05 | −17.24 | 116.58 | 0.9201 |

The first and second columns of Table 3 contain the compared ND's. The fourth column shows the mean difference between the compared samples. The third and fifth columns show the lower and upper limits for 95% confidence intervals for the true mean difference. The sixth column contains the p-value for a hypothesis test that the corresponding mean difference between the compared samples is equal to zero.

The ADV thresholds in the LBL models as a function of mechanical index needs are also addressed. As shown in FIG. 8A-8B, the activation profiles of all the samples appear to be quite similar. Tables 2 and 3 reiterate this notion by fitting the ADV vs MI profiles of the samples (i.e. Slope DFB-ND's=284.30±30.51, LBL$_6$-NDs=290.16±28.96, and LBL$_{10}$-NDs=307.39±33.53; where the p-values of LBL$_6$-NDs and LBL$_{10}$-NDs compared to DFB-ND's were 0.9894 and 0.8670 respectively). The data presented in FIGS. 8A-8B, Table 2, and Table 3 suggests that the layering process has no notable effect on the ADV thresholds of the particle.

It should be emphasized that the above-described embodiments of the present disclosure are merely possible examples of implementations and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

REFERENCES

Gramiak, R.; Shah, P. M. Echocardiography of the aortic root. *Invest Radiol.* 1968, 3, 356-66.

Roelandt, J. Contrast Echocardiography. *Ultrasound Med Biol,* 1982, 8, 471-92.

Becher, H., & Gibson, P. (2013). Contrast Echocardiography: Current Applications and Future Perspectives. *Current Cardiovascular Imaging Reports,* 6(6), 473-485.

Senior, R., Becher, H., Monaghan, M., Agati, L., Zamorano, J., Vanoverschelde, J., & Nihoyannopoulos, P. (2009). Contrast echocardiography: Evidence-based recommendations by European Association of Echocardiography. *European Journal of Echocardiography,* 10(2), 194-212.

Kripfgans, O. D., Fowlkes, J. B.; Woydt, M.; Eldevik O. P.; Carson, P. L. *In vivo droplet vaporization for occlusion therapy and phase aberration correction. IEEE Trans Ultrason Ferroelectr Freq Control.* 2002. 49, 726-738.

Kripfgans, O. D.; Fowlkes, J. B.; Miller, D. L.; Oldevik, O. P.; Carson, P. L. Acoustic Droplet Vaporization for Therapeutic and Diagnostic Applications. *Ultrasound Med. Biol.* 2000, 26, 1177-89.

Christensen-Jeffries, K., Couture, O., Dayton, P., Eldar, Y., Hynynen, K., Kiessling, F. Van Sloun, R. (2020). Super-resolution Ultrasound Imaging. *Ultrasound in Medicine & Biology,* 46(4), 865-891.

Choi, J., Kim, H.-Y., Ju, e. J., Jung, J., Park, J., Chung, H.-K., . . . Choi, E. K. (2012, March 5). Use of macrophages to deliver therapeutic and imaging contrast agents to tumors. *Biomaterials.* 2012. 33, 4125-4203.

Fabiilli, M., Haworth, K., Sebastian, I., Kripfgans, O., Carson, P., & Fowlkes, J. (2010). Delivery of Chlorambucil Using an Acoustically-Triggered Perfluoropentane Emulsion. *Ultrasound in Medicine & Biology,* 36(8), 1364-1375.

Marshalek, J. P.; Sheeran, P. S.; Ingram, P.; Dayton, P. A.; Witte, R. S.; & Matsunaga, T. O. Intracellular delivery and ultrasonic activation of folate receptor-targeted phase-change contrast agents in breast cancer cells in vitro. *J Control Release.* 2016, 243, 69-77.

Rapoport, N., Kennedy, A., Shea, J., Scaife, C., & Nam, K. (2009). Controlled and targeted tumor chemotherapy by ultrasound-activated nanoemulsions/microbubbles. *Journal of Controlled Release,* 138(3), 268-276.

Choudhury, S. A; Xie, F.; Dayton, P. A.; Porter, T. R. Acoustic Behavior of a reactivated, Commercially Available Ultrasound Contrast Agent. *J Am Soc Echocardiogr.* 2018, 30, 189-197.

Matsunaga, T. O.; Sheeran, P. S.; Luois, S.; Streeter, J. E.; Mullin, L. B.; Banerjee, B.; Dayton, P. A. Phase-Change Nanodroplets Using Highly Volatile Perfluorocarbons: Toward a Platform for Extravascular Ultrasound Imaging. *Theranostics* 2012, 12, 1185-1198.

Sheeran, P. S.; Wong, V. P.; McFarland, R. J.; Ross, W. D.; Feingold, S.; Matsunaga, T. O.; Dayton, P. A. Decafluorobutane as a phase-change contrast agent for low-energy extravascular ultrasound imaging. *J. Ultr. Med. Biol.* 2011; 37, 1518-1530.

Martin, A.; Homenick, C.; Xiang, Y.; Gillies, E.; & Matsuura, N. Polyelectrolyte Coatings Can Control Charged Fluorocarbon Nanodroplet Stability and Their Interaction with Macrophage Cells. *Langmuir: The ACS Journal of Surfaces and Colloids.* 2019, 35, 4603-4612.

Lentacker, I., De Geest, B., Vandenbroucke, R., Peeters, L., Demeester, J., De Smedt, S., & Sanders, N. (2006). Ultrasound-responsive polymer-coated microbubbles that bind and protect DNA. *LANGMUIR,* 22(17), 7273-7278.

Reznik, N., Williams, R., & Burns, P. (2011). Investigation of Vaporized Submicron Perfluorocarbon Droplets as an Ultrasound Contrast Agent. *Ultrasound in Medicine & Biology,* 37(8), 1271-1279.

Yasu, T., Schmid-Schönbein, G., Cotter, B., & Demaria, A. (1999). Flow dynamics of QW7437, a new dodecafluoropentane ultrasound contrast agent, in the microcirculation. *Journal of the American College of Cardiology,* 34(2), 578-586.

Maeda, H., Wu, J., Sawa, T., Matsumura, Y., & Hari, K. (2000). Tumor vascular permeability and the EPR effect in macromolecular therapeutics: A review. *Journal of Controlled Release,* 65(1-2), 271-284.

Lin, S.; Zhang, G.; Leow, C. H.; Tang, M. X. Effects of microchannel confinement on acoustic vaporization of ultrasound phase change contrast agents. *Phys. Med. Biol.* 2017. 62, 6884-6898.

Ee, S. L., Duan, Xiumei, Liew, Jeffrey, & Nguyen Q. D. (2007, December 12). Droplet Size and Stability of Nanoemulsions Produced by the Temperature Phase Inversion Method.

Lentacker, I.; De Geest, B. G.; Vandenbroucke, R. E.; Peeters, L.; Demeester, J.; De Smedt, S. C.; Sanders, N. N. Ultrasound-responsive polymer-coated microbubbles that bind and protect DNA. *Langmuir.* 2006. 22, 7273-7278.

Singh, R., Husseini, G. A., & Pitt, W. G. Phase transitions of nanoemulsions using ultrasound: Experimental observations. *Ultrason Sonochem.* 2012. 19, 1120-1125.

Sheeran, P. S.; Luois, S.; Dayton, P. A.; Matsunaga, T. O. Formulation and Ultrasound Studies of a New Pro-bubble (Phase-Shift agent) for Activation with Low Acoustic Intensities. *Langmuir.* 2011, 27, 10412-10420.

Marshalek, J. P.; Sheeran, P. S.; Ingram, P.; Dayton, P. A.; Witte, R. S.; Matsunaga, T. O.; *Intracellular delivery and ultrasonic activation of folate receptor-targeted phase-change contrast agents in breast cancer cells in vitro. J Control Release.* 2016, 243, 69-77.

Hadinger, K. P.; Marshalek, J. P.; Sheeran, P. S.; Dayton, P. A.; Matsunaga, T. O.; "Optimization of Phase-Change Contrast Agents for Targeting MDA-MB-231 Breast Cancer Cells", *Ultrasound in Medicine & Biology.* 2018, 44, 2728-2738.

Choudhury, S. A.; Xie, F.; Dayton, P. A.; Porter, T. R. Acoustic Behavior of a reactivated, Commercially Available Ultrasound Contrast Agent. 2017. *J. Am. Soc. Echocardiogr.* 30, 189-197.

Sheeran, P. S.; Matsuura, N.; Borden, M. A.; Williams, R.; Matsunaga, T. O.; Burns, P. N.; Dayton, P. A. Methods of Generating Submicrometer Phase-Shift Perfluorocarbon Droplets for Applications in Medical Ultrasonography. *IEEE Trans Ultrason Ferroelectr Freq Control.* 2017, 64, 252-263.

Yoo, K.; Walker, W. R.; Williams, R.; Tremblay-Darveau, C.; Burns, P. N.; Sheeran, P. S. Impact of Encapsulation on in vitro and in vivo Performance of Volatile Nanoscale Phase-Shift Perfluorocarbon Droplets Ultrasound *Med. Biol.* 2018, 44, 1836-1852.

Huang, Y.; Vezeridis, A. M.; Wang, J.; Wang, Z.; Thompson, M.; Mattrey, R. F.; Gianneschi, N. C. Polymer-Stabilized Perfluorobutane Nanodroplets for Ultrasound Imaging Agents. *J. Am. Chem. Soc.* 2017. 139, 15-18.

Toumia, Y.; Cerroni, B.; Domenici, F.; Lange, H.; Bianchi, L.; Cociorb, M.; Brasili, F.; Chiessi, E.; D'Agostino, E.; Van Den Abeele, K.; Heymans, S. V.; D'Hooge, J.; Paradossi, G. *Phase Change Ultrasound Contrast Agents with a Photopolymerized Diacetylene Shell. Langmuir.* 2019, 35, 10116-10127.

de Leon, A.; Perera, R.; Hernandez, C.; Cooley, M.; Jung, O.; Jeganathan, S.; Abenojar, E.; Fishbein, G.; Sojahrood, A. J.; Emerson, C. C.; Stewart, P. L.; Kolios, M. C.; Exner, A. A. Contrast enhanced ultrasound imaging by nature-inspired ultrastable echogenic nanobubbles. *Nanoscale.* 2019, 11, 15647-15658.

Yarmoska, S., Yoon, H., & Emelianov, S. (2019). Lipid Shell Composition Plays a Critical Role in the Stable Size Reduction of Perfluorocarbon Nanodroplets. *Ultrasound in Medicine & Biology,* 45(6), 1489-1499.

Sheeran, P. S.; Luois, S. H.; Mullin, L. B.; Matsunaga, T. O., Dayton, P. A. Design of ultrasonically-activatable nanoparticles using low boiling point perfluorocarbons. *Biomaterials.* 2012. 33, 3262-3269.

de Gracia Lux, C.; Vezeridis, A. M.; Lux, J.; Armstrong, A. M.; Sirsi, S. R.; Hoyt, K.; Mattrey, R. F. Novel method for the formation of monodisperse superheated perfluorocarbon nanodroplets as activatable ultrasound contrast agents. *RSC Adv.* 2017, 48561-48568.

Ghorbani, M.; Olofsson, K.; Benjamins, J.; Loskutova, K.; Paulraj, T.; Wiklund, M.; Svagan, A. Unravelling the Acoustic and Thermal Responses of Perfluorocarbon Liquid Droplets Stabilized with Cellulose Nanofibers. *Langmuir: The ACS Journal of Surfaces and Colloids.* 2019, 35, 13090-13099.

Ramasamy, T.; Haidar, Z. S.; Tran, T. H.; Choi, J. Y.; Jeong, J. H.; Shin, B. S.; Choi, H. G.; Yong, C. S.; Kim, J. O. Layer-by-layer assembly of liposomal nanodroplets with PEGylated polyelectrolytes enhances systemic delivery of multiple anticancer drugs. *Acta Biomater.* 2014, 10, 5116-5127.

Shakya, G., Hoff, S., Wang, S., Heinz, H., Ding, X., & Borden, M. (2020). Vaporizable endoskeletal droplets via tunable interfacial melting transitions. *Science Advances,* 6(14), Eaaz7188.

What is claimed is:

1. A nanodroplet comprising a core comprising gas phase-change contrast agent (PCCA) and a shell membrane consisting of an anionic lipid and a cationic lipid with layer-by-layer (LBL) alternating positive and negatively charged biopolymer layers attached thereon, wherein said nanodroplet increases thermal stability yet retains acoustic activation requirement.

2. The nanodroplet of claim 1, wherein the gas PCCA is decafluorobutane (DFB).

3. The nanodroplet of claim 1, wherein the LBL biopolymer layers comprise six (6) alternating positive and negative charged biopolymer layers.

4. The nanodroplet of claim 1, wherein the LBL biopolymer comprise ten (10) alternating positive and negative charged biopolymer layers.

5. The nanodroplet of claim 2, wherein the LBL biopolymer layers comprise up to twenty (20) alternating positive and negative charged biopolymer layers.

6. The nanodroplet of claim 2, wherein the LBL biopolymer layers comprises alternating PLL and PEG-b-PLD biopolymer layers.

7. A nanodroplet comprising:

a) a gaseous perfluorocarbon core;

b) a shell membrane consisting of 1,2-dipalmitoyl phosphatidylcholine (DPPC) and dimethyldioctadecyl ammonium bromide (DDAB); and c) layer-by-layer (LBL) alternating positively and negatively charged biopolymer layers attached to the shell membrane.

8. The nanodroplet of claim 7, wherein the gaseous perfluorocarbon core comprises decafluorobutane (DFB) gas phase-change contrast agent (PCCA).

9. The nanodroplet of claim 8, wherein the LBL biopolymer layers comprise at least two, three, four, five, six, seven, eight, night, and ten alternating positive and negative charged biopolymer layers.

10. The nanodroplet of claim 9, wherein the LBL biopolymer layers comprise six (6) alternating positive and negative charged biopolymer layers.

11. The nanodroplet of claim 9, wherein the LBL biopolymer layers comprise ten (10) alternating positive and negative charged biopolymer layers.

12. The nanodroplet of claim 9, wherein the LBL biopolymer layers comprises alternating PLL and PEG-b-PLD biopolymer layers.

13. The nanodroplet of claim 7, wherein the LBL biopolymer layers comprise up to twenty (20) alternating positive and negative charged biopolymer layers.

14. A method of making the nanodroplet of claim 1, comprising generating nanodroplet comprising the core and the shell, and then alternating and dispersing positively and negatively charged biopolymer layer-by-layer (LBL) onto the shell of the nanodroplet via electrostatic interactions.

15. The method of claim 14, wherein the core comprises gaseous perfluorocarbon comprising decafluorobutane (DFB) gas phase-change contrast agent (PCCA), and wherein the shell comprises DPPC/DDAB.

16. The method of claim 15 wherein the LBL biopolymer layers comprises alternating PLL and PEG-b-PLD biopolymer layers.

17. The method of claim 16, wherein the LBL biopolymer layers comprise at least two, three, four, five, six, seven, eight, night, and ten alternating positive and negative charged biopolymer layers.

18. The method of claim 17, wherein the LBL biopolymer layers comprise six (6) alternating positive and negative charged biopolymer layers.

19. The method of claim 17, wherein the LBL biopolymer layers comprise ten (10) alternating positive and negative charged biopolymer layers.

20. The nanodroplet of claim 1, wherein the anionic lipid is 1,2-dipalmitoyl phosphatidylcholine (DPPC) and the cationic lipid is dimethyldioctadecyl ammonium bromide (DDAB).

* * * * *